United States Patent [19]

Kane

[11] 4,296,035
[45] Oct. 20, 1981

[54] TOTAL SYNTHESIS OF THE UTERO-EVACUANT SUBSTANCE D,L-ZOAPATANOL

[75] Inventor: Vinayak V. Kane, Princeton, N.J.

[73] Assignee: Ortho Pharmaceutical Corporation, Raritan, N.J.

[21] Appl. No.: 130,660

[22] Filed: Mar. 17, 1980

Related U.S. Application Data

[62] Division of Ser. No. 971,471, Dec. 20, 1979, Pat. No. 4,237,053.

[51] Int. Cl.³ .......................................... C07D 313/04
[52] U.S. Cl. ................................................... 260/333
[58] Field of Search ....................................... 260/333

[56] References Cited

U.S. PATENT DOCUMENTS 4,060,604 11/1977 Kanojia ............................... 424/278
4,086,358  4/1978 Wachter et al. ..................... 424/278
4,112,078  9/1978 Chen .................................... 424/278

Primary Examiner—Norma S. Milestone
Attorney, Agent, or Firm—Benjamin F. Lambert

[57] ABSTRACT

A method for the synthesis of racemic 2S* 3R*-6E-(2''-hydroxyethylidene)-2-methyl-2-(4',8'-dimethyl-5'-oxo-7'-nonenyl)-oxepan-3-ol is described. The naturally occurring product, 2S,3R-6E-(2''-hydroxyethylidene)-2-methyl-2-(4',8'-dimethyl-5'-oxo-7'-nonenyl)-oxepan-3-ol, is one of the active components of the zoapatle plant.

3 Claims, No Drawings

TOTAL SYNTHESIS OF THE UTERO-EVACUANT SUBSTANCE D,L-ZOAPATANOL

This is a division, of application Ser. No. 971,471, filed Dec. 20, 1979, now U.S. Pat. No. 4,237,053.

The zoapatle plant is a bush about two meters high that grows wild in Mexico. Botanically, it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, Third Edition, Ediciones Botas (1944).

The plant has been used for centuries in the form of a "tea" or other crude aqueous preparations primarily as a labor inducer or menses inducer for women. Its use as a utero-evacuant has been documented in the literature.

In U.S. Pat. No. 4,086,358, a method is described for the isolation of the active ingredients in the zoapatle plant. One of the active ingredients is 2S, 3R-6E-(2-hydroxyethylidene)-2-methyl-2-(4,8-dimethyl-5-oxo-7-nonenyl)-oxepan-3-ol. This compound, referred to as zoapatanol, has the following structural formula:

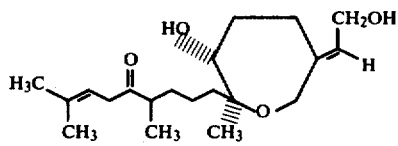

The present invention relates to a method for the total synthesis of 2S*,3R*-6E-(2-hydroxyethylidene)-2-methyl-2-(4',8'-dimethyl-5'-oxo-7'-nonenyl)-oxepan-3-ol and 2S*,3R*-6Z-(2-hydroxyethylidene)-2-methyl-2-(4',8'-dimethyl-5'-oxo-7'-nonenyl)-oxepan-3-ol.

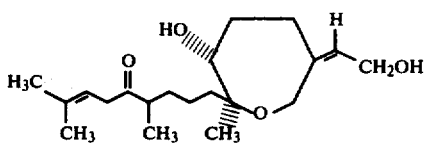

The asterisk in the name (e.g. 2S*,3R*) indicates the racemic nature of the compound and thus refers to the relative configuration of the chiral centers. The lettering of the appropriate positions corresponds to that of the naturally occurring optical isomer 28 (e.g. 2S,3R).

Many of the intermediates employed in the synthesis of zoapatanol are novel compounds and are included as part of the invention.

The synthesis is comprised of several steps which are summarized in the following schematic diagram:

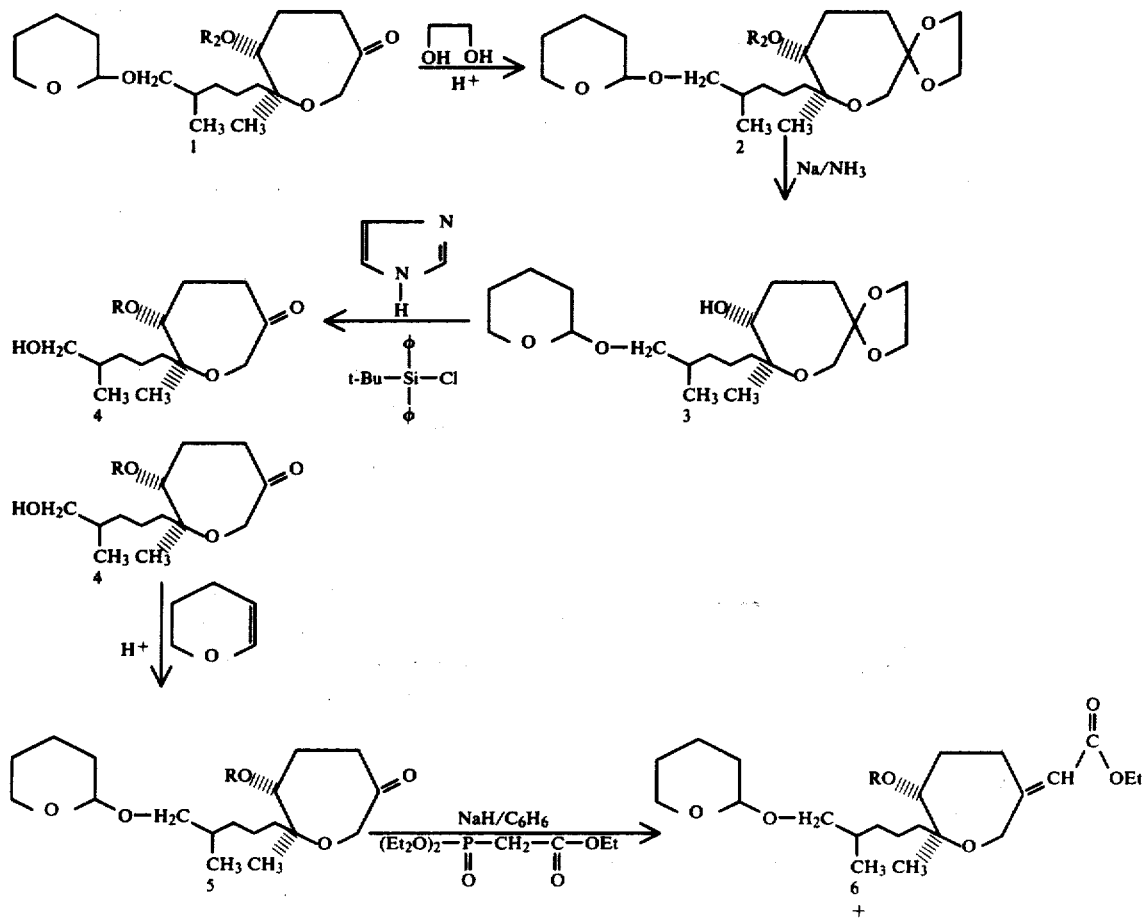

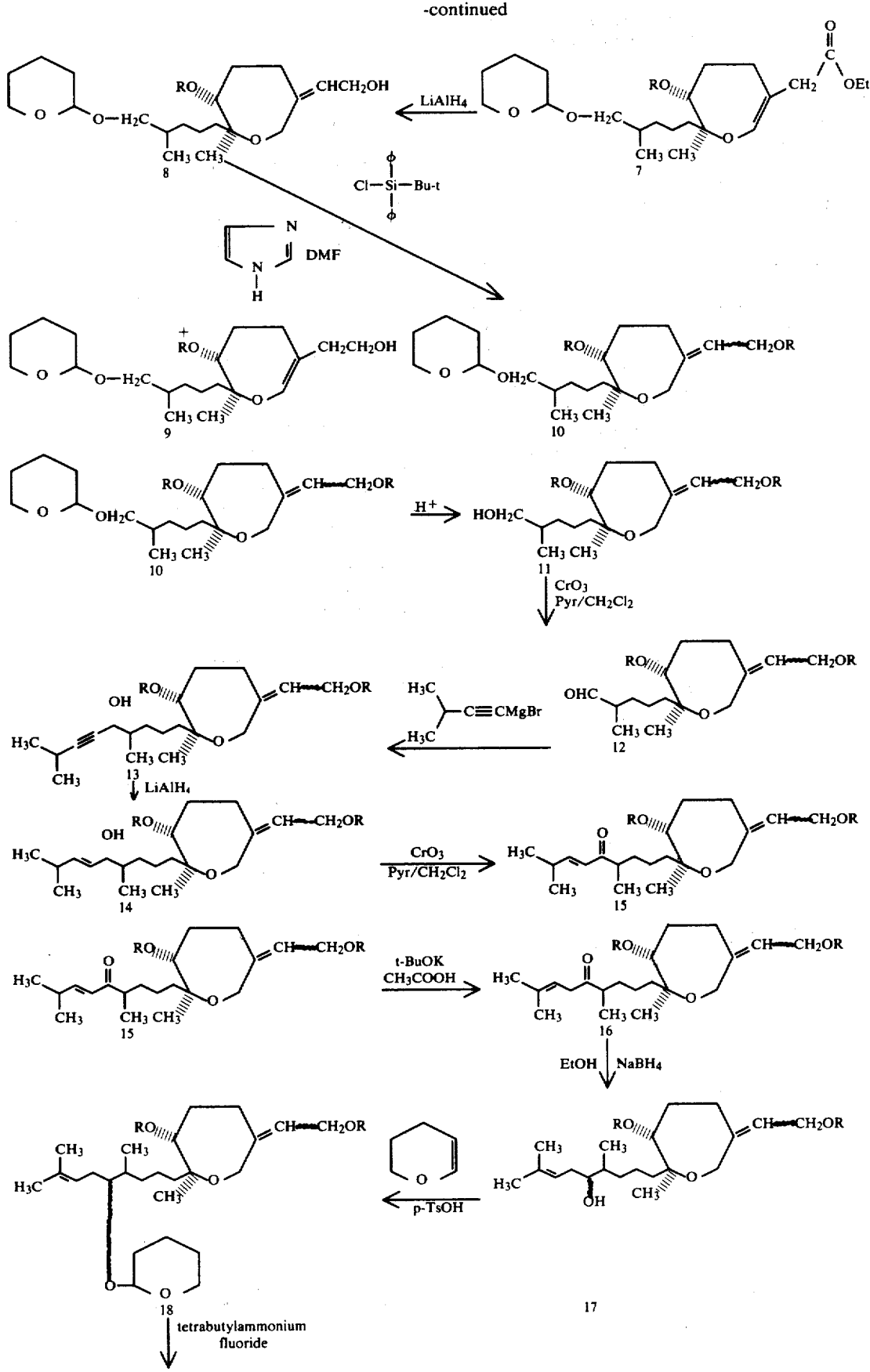

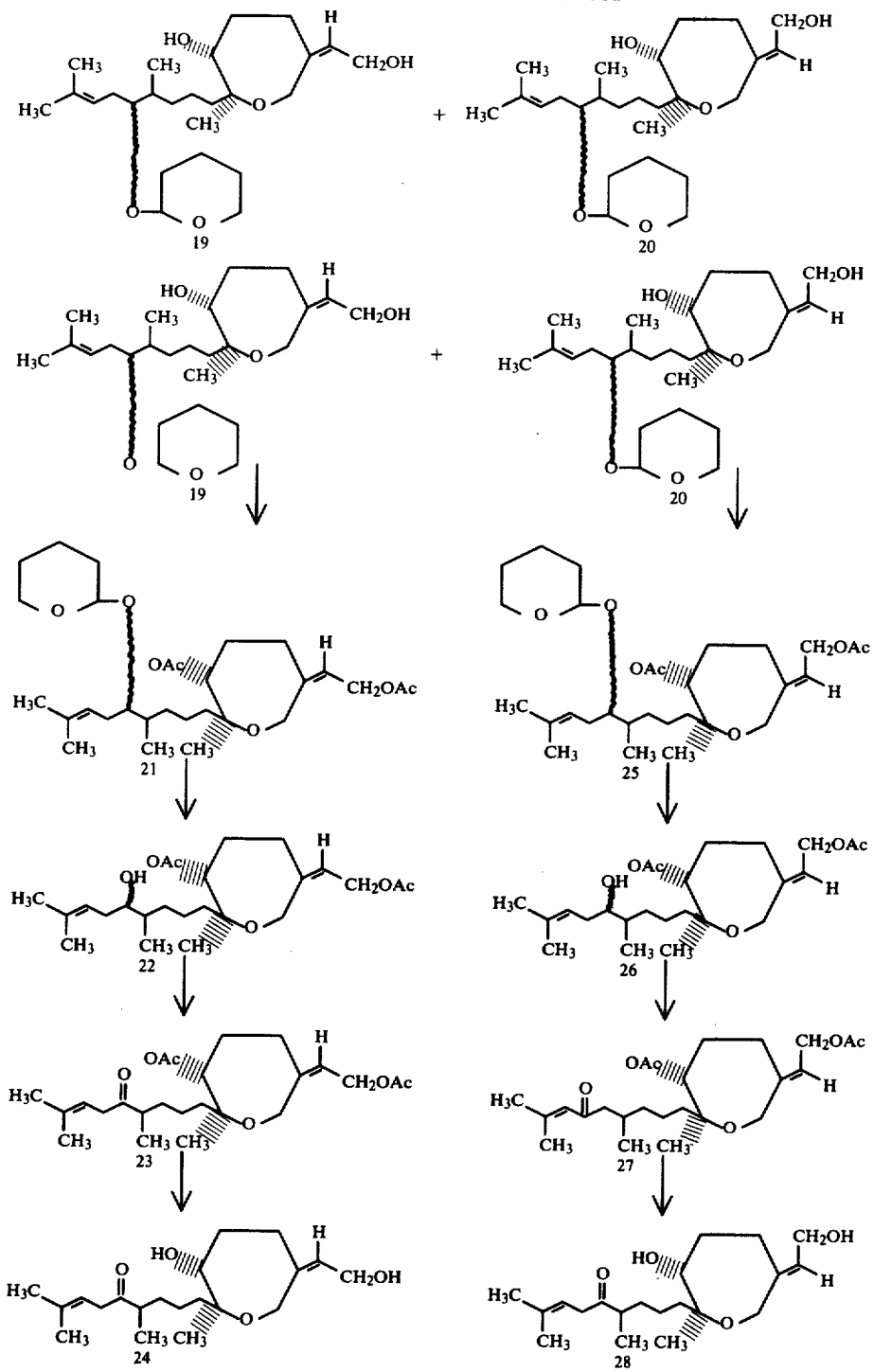

In the above diagram, the symbols Ph, p-TsOH, Ac, EtOH, DMF, Et and Bu stand for phenyl, p-toluenesulfonic acid, acetyl, ethanol, dimethylformamide, ethyl and butyl respectively and R is a t-butyldiphenylsilyl group.

The starting material in the synthesis is 3-benzyloxy-2-methyl-2-(4'-methyl-5'-(tetrahydropyran-2''-yloxy)-pentyl-oxepan-6-one (1). As seen from the diagram in the first step in the synthesis, the ketone (1) is converted to a ketal (2) by reaction with ethylene glycol. The reaction is carried out at elevated temperatures, preferably the reflux temperature of the solvent in the presence of a catalyst such as, for example p-toluenesulfonic acid. Suitable solvents which can be employed include benzene and toluene. The compound (2) is collected and purified by techniques known to those skilled in the art and then converted to an alcohol (3) by reaction with sodium in liquid ammonia. The reaction is preferably carried out in an inert atmosphere such as argon or nitrogen, for example. The alcohol (3) is separated from the reaction mixture, purified by techniques known to those skilled in the art and then converted to the corresponding t-butyldiphenylsilyloxy derivative (4) by reaction with t-butyldiphenylsilyl chloride in a suitable solvent such as dimethylformamide or benzene in the presence of imidazole. The reaction is preferably carried out at the reflux temperature of the solvent. The tetrahydropyranyl and the ketal protecting groups are removed during the reaction; the hydroxyl group is reprotected by reacting the t-butyldiphenylsilyloxy derivative with dihydropyran. The reaction is preferably carried out in a solvent such as ether or methylene chloride at room temperature and in an inert atmosphere such as nitrogen. p-Toluenesulfonic acid or camphorsulfonic acid is added as a catalyst. The tetrahydropyranyl ketone (5) upon reaction with triethylphosphonoacetate in the presence of an alkali metal hydride such as sodium hydride or potassium hydride, is converted to a mixture of carboethoxymethylidene double bond isomers (6 and 7). The reaction is carried out in a suitable solvent such as benzene in the presence of sodium hydride. Temperatures between room temperature and about 100° C. may be employed and the reaction is preferably carried out in an inert atmosphere such as nitrogen or argon. The mixture is purified by techniques known to those skilled in the art and is then converted to a mixture of alcohols (8 and 9) by reaction with a reducing agent such as lithium aluminum hydride. The reaction is preferably carried out in a solvent such as diethyl ether or tetrahydrofuran at the reflux temperature of the solvent in an inert atmosphere such as nitrogen. The diols (8 and 9) are separated by chromatography using silica gel as the adsorbent in hexane. The diol (8) is then converted to the t-butyldiphenylsiloxy derivative (10) by reaction with t-butyldiphenylsilyl chloride in dimethylformamide in the presence of imidazole. The reaction is preferably carried out in a suitable solvent at room temperature in an inert atmosphere. The t-butyldiphenylsilyl derivative (10) is separated and purified by techniques known to those skilled in the art. The tetrahydropyranyl group is then removed by reaction of the t-butyldiphenylsilyl derivative (10) with an organic acid such as acetic acid, for example, to form the alcohol (11) which is then oxidized to the corresponding aldehyde (12) by reaction with an oxidizing agent such as chromium trioxide/pyridine in a suitable solvent such as methylene chloride. The side chain in the molecule is extended by reacting the aldehyde (12) with an acetylenic Grignard reagent such as that prepared from 3-methyl-1-butyne. The resulting acetylenic compound (13) is then converted to the olefinic compound (14) by reduction with lithium aluminum hydride. The reduction is preferably carried out in an anhydrous solvent such as tetrahydrofuran or ether in an inert atmosphere such as nitrogen or argon. The allylic hydroxyl group in the side chain is converted to a keto group by reaction with an oxidizing agent such as chromium trioxide/pyridine in methylene chloride or with manganese dioxide in methylene chloride or chloroform. The unsaturated ketone (15) is converted to a $\beta,\gamma$ unsaturated ketone (16) by reaction with potassium-t-butoxide in butanol followed by treatment with an organic acid such as acetic acid. The reaction is preferably carried out at room temperature in an inert atmosphere much as nitrogen, for example. The $\beta,\gamma$ unsaturated ketone (16) is then reduced to the alcohol (17) by reaction with a suitable reducing agent such as sodium borohydride in a suitable solvent such as ethanol. The alcohol (17) is then converted to the corresponding tetrahydropyranyl derivative (18) by reaction with dihydropyran in the presence of p-toluenesulfonic acid in a suitable solvent such as ether. The tetrahydropyranyl derivative (18) is then converted to a mixture of diols (19 and 20) by reaction with tetrabutylammonium fluoride in a suitable solvent such as tetrahydrofuran.

The diols are separated by methods known to those skilled in the art. Column chromatography on an adsorbent material such as silica gel is a preferred method. The diols (19,Z isomer and 20,E isomer) each contain all of the 20 carbon atoms present in zoapatanol (E-isomer). A four step sequence converts the diols (19 and 20) to racemic zoapatanol (28) and to the racemic Z isomer (24).

The first step in the synthesis of the naturally occurring isomer (28) from the diol (20) involves the preparation of the corresponding diester (25). The diester (25) is prepared by conventional means from a lower alkyl anhydride or alkanoyl halide such as, for example, acetic anhydride or acetyl chloride in the presence of a base such as pyridine. The tetrahydropyranyl protecting group is removed by treating the diester (25) with an organic acid such as acetic acid, p-toluenesulfonic acid or camphorsulfonic acid in a suitable solvent mixture such as tetrahydrofuran-water, for example. The alcohol (26) which forms is then oxidized to the corresponding ketone (27) with an oxidizing agent such as chromium trioxide/pyridine. Reaction of the ketone (27) with tetrabutylammonium hydroxide in a suitable solvent such as methanol yields racemic zoapatanol. The same series of reactions when carried out on the isomeric diol (19) leads to the Z isomer (24).

As employed herein, R is a t-butyldiphenylsilyl group, $R_1$ is a lower alkanoyl group having 2-5 carbon atoms such as an acetyl, propionyl or butyryl group and $R_2$ is selected from the group consisting of benzyl, p-nitrobenzyl and p-methylbenzyl.

The following describes the invention in greater particularity and is intended to be a way of illustrating but not limiting the invention.

EXAMPLE 1

(2S*,3R*)-3-Benzyloxy-2-methyl-2-[4'-methyl-5'-(tetrahydropyran-2''-yloxy)-pentyl]-oxepan-6-one (1)

A solution of pyridine (5.4 g, 0.0686 mol) and chromium trioxide (3.4 g, 0.0343 mol) in methylene chloride (150 ml) at 23° in a nitrogen atmosphere is stirred for 45 minutes. The mixture is cooled to −10° and celite (20 g) is added followed by the alcohol 2S*,3R*-3-benzyloxy-2-methyl-2-[4'-methyl-5'-(tetrahydropyran-2''-yloxy)-pentyl]-oxepan-6-ol (2.4 g, 0.0057 mol) in methylene chloride (50 ml). After stirring for 2 hours at 0°, the mixture is filtered and the celite cake is washed with methylene chloride (10×50 ml). The filtrate and the washings are combined and washed with saturated sodium bicarbonate (2×100 ml), dried (MgSO$_4$) and evaporated in vacuo. The crude product (2.8 g) is chromatographed on SilicAR CC-7 (40 g, Mallinckrodt) in hexane. Elution with 10% ethyl acetate/hexane gives (2S*,3R*)-3-benzyloxy-2-methyl-2-[4'-methyl-5'-(tetrahydropyran-2''-yloxy)-pentyl]-oxepan-6-one as a clear colorless oil (2.1 g, 88%): nmr (CDCl$_3$)δ 1.00 (d, J=6 Hz, 3H, -CH-C$\underline{H}_3$), 1.30 (s, 3H, C$\underline{H}_3$), 2.60 (m, 2H, -CO-CH$_2$-C$\underline{H}_2$-), 3.98 (m, 2H, -O-C$\underline{H}_2$-CO-), 4.50 (d of d, J=10 Hz, 2H, -O-C$\underline{H}_2$Ph), 4.60 (broad s, 1H, -O-C$\underline{H}$-O-), 7.2 (s, 5H, aromatic).

EXAMPLE 2

(2S*,3R*)-3-Benzyloxy-6,6-ethylenedioxy-2-methyl-2-[4'-5'-(tetrahydropyran-2" -yloxy)-pentyl]-oxepane (2)

A mixture of (2S*,3R*)-3-benzyloxy-2-methyl-2-[4'-methyl-5'-(tetrahydropyran-2"-yloxy)-pentyl]-oxepan-6-one (2.1 g, 0.005 mol), ethylene glycol (10 ml) and p-toluenesulfonic acid (350 mg) in benzene (75 ml) is refluxed for 20 hours using a Dean-Stark apparatus. The solution is cooled and diluted with water (150 ml) and ether (150 ml). The organic layer is separated and the aqueous layer is extracted with ether (2×250 ml). The combined organic layers are washed with saturated sodium bicarbonate solution (2×50 ml), saturated sodium chloride solution and dried (MgSO4). The solvents are removed at reduced pressure and the crude product (2.7 g) is chromatographed on SilicAR CC-7 (50 g, Mallinckrodt) in hexane. Elution with 2–20% EtOAc/hexane gives (2S*,3R*)-3-benzyloxy-6,6-ethylenedioxy-2-methyl-2-[4'-methyl-5'-(tetrahydropyran-2"-yloxy-pentyl]-oxepane (0.215 g); nmr (CDCl3)δ 3.35

(m, 7H, —CH2—O—CH—O—CH2—,

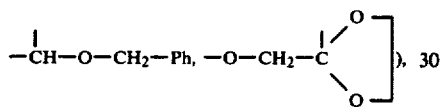

—CH—O—CH2—Ph, —O—CH2—C ), 30

3.9 (s, 4H, ketal), 4.4

(m, 3H, —O—CH—O—CH2—,

-O-CH2-Ph), 7.25 (s, 5H, aromatic).

EXAMPLE 3

(2S*,3R*)-6,6-Ethylenedioxy-3-hydroxy-2-methyl-2-[4'-methyl-5'-(tetrahydropyran-2"-yloxy)-pentyl]-oxepane (3)

t-Butyl alcohol (0.222 g, 0.003 mol) is added to a freshly distilled solution of ammonia (12 ml) cooled to −78° in an argon atmosphere. The cooling bath is removed and (2S*,3R*)-3-benzyloxy-6,6-ethylenedioxy-2-methyl-2-[4'-methyl-5'-(tetrahydropyran-2"-yloxy)-pentyl]-oxepane (0.215 g, 0.000465 mol) in tetrahydrofuran (3 ml) is added. Freshly cut sodium metal (0.024 g, 0.001 mol) is added in small pieces at −33° C. The resulting blue solution is stirred for 0.25 hours and quenched by adding ether (20 ml) followed by water (25 ml). The ammonia is evaporated at 23° C. and the ether layer is separated. The water phase is extracted with ether (3×25 ml). The ether phases are combined, washed with a saturated sodium chloride solution, dried (MgSO4) and the solvent is removed under reduced pressure to give a crude yellow oil (0.210 g). This material is chromatographed on SilicAR CC-7 (4 g, Mallinckrodt) in hexane. Elution with 2–25% EtOAc/hexane gives (2S*,3R*)-6,6-ethylenedioxy-3-hydroxy-2-methyl-2-[4'-methyl-5'-(tetrahydropyran-2"-yloxy)-pentyl]-oxepane as a clear oil (0.170 g): ir (neat) 3335 cm−1 (—OH).

EXAMPLE 4

(2S*,3R*)-3-t-Butyldiphenylsilyloxy-2-methyl-2-(4'-methyl-5'-hydroxypentyl)-oxepan-6-one (4)

(2S*,3R*)-6,6-Ethylenedioxy-3-hydroxy-2-methyl-2-[4'-methyl-5'-(tetrahydropyran-2"-yloxy)-pentyl]-oxepane (0.150 g, 0.004 mol) is added to a suspension of sodium hydride (0.038 g, 0.0008 mol, of a 50% mineral oil dispersion freshly washed with hexane and benzene) in benzene (2 ml) at 23° C. in a nitrogen atmosphere. The mixture is stirred for 1 hour, t-butyldiphenylsilychloride (0.22 g, 0.0008 mol) in benzene (0.5 ml) is added and the mixture is heated to reflux at 80° C. The mixture is refluxed for 3 days then cooled to 23° C. and washed with a saturated sodium bicarbonate solution. The aqueous phase is extracted with ether (2×25 ml). The organic layers are combined, dried (MgSO4) and the solvents are removed at reduced pressure to give 0.205 g of crude product. The crude product is chromatographed on SilicAR CC-7 (3.0 g, Mallinckrodt) in hexane. Elution with 10% ethyl acetate gives (2S*,3R*)-3-t-butyldiphenylsilyloxy-2-methyl-2-(4'-methyl-5'-hydroxypentyl)-oxepan-6-one (0.122 g): nmr (CDCl3)δ 1.1 (s, 9H, t-butyl), 3.4

(m, 3H, HO—CH2—CH—, —CH—O—Si—), 4.0 (m, 2H, —O—CH2—C=O), 7.5 (m, 10H, aromatic).

EXAMPLE 5

(2S*,3R*)-3-t-Butyldiphenylsilyloxy-2-methyl-2-[4'-methyl-5'-(tetrahydropyran-2"-yloxy)-pentyl]oxepan-6-one (5)

A mixture of the alcohol (2S*,3R*)-3-t-butyldiphenylsilyloxy-2-methyl-2-(4'-methyl-5'-hydroxypentyl)-oxepan-6-one (0.11 g, 0.000228 mol), dihydropyran (0.038 g, 0.000456 mol) and p-toluenesulfonic acid (3 crystals) in anhydrous ether (3 ml) is stirred at 23° C. under a nitrogen atmosphere for 18 hours. The mixture is diluted with ether (10 ml), washed with saturated sodium bicarbonate, water and saturated sodium chloride, dried (MgSO4) and evaporated under reduced pressure to give the crude product. The crude product is chromatographed on SilicAR CC-7 (2 g, Mallinckrodt) in hexane. Elution with ethyl acetate/hexane gives (2S*,3R*)-3-t-butyldiphenylsilyloxy-2-methyl-2-[4'-methyl-5'-(tetrahydropyran-2"-yloxy)-pentyl]-oxepan-6-one as a colorless oil (0.105 g): nmr (CDCl3)δ 2.35

(t, 2H, —CH2—CH2—C=O), 3.35 (m, 7H,

—CH2—O—CH—O—CH2—, —O—CH2—C=O,

—CH—O—Si—), 4.5 (s, 1H, —O—CH—O—CH2—).

EXAMPLE 6

(2S*,3R*)-3-t-Butyldiphenylsilyloxy-6-(2'-carboethoxymethylidene)-2-methyl-2-[4'-methyl-5'-(tetrahydropyran-2''-yloxy)-pentyl]-oxepane (6) and (2S*,3R*)-3-t-butyldiphenylsilyloxy-6-(2'-carboethoxymethyl)-2-methyl-2-[4'-methyl-5'-(tetrahydropyran-2''-yloxy)-pentyl]-6-oxepene (7)

Triethylphosphonoacetate (125 mg, 0.557 mmole) in benzene (3 ml) is added to a suspension of sodium hydride (27 mg, 0.557 mmole, of a 50% mineral oil dispersion freshly washed with hexane and benzene) in benzene (2 ml) in a nitrogen atmosphere. The mixture is heated to 70° C. and stirred for 15 minutes. The mixture is then cooled to 25° C. and (2S*,3R*)-3-t-butyldiphenylsilyloxy-2-methyl-2-[4'-methyl-5'-(tetranydropyran-2''-yloxy)-pentyl]-oxepan-6-one (105 mg, 0.186 mmole) in benzene is added. The mixture is heated to 70° C. and stirred for 1 hour. The reaction mixture is then cooled to 25° C. and diluted with ether (10 ml) and quenched with water. The mixture is poured into pH 7 phosphate buffer (25 ml) and extracted with ether (5×25 ml). The organic layers are combined, dried (MgSO4) and evaporated to give 121 mg of a yellow oil. This material is chromatographed on SilicAR CC-7 (2 g, Mallinckrodt) in hexane. Elution with 25% ethyl acetate/hexane gives 85 mg of a colorless oil whose nmr indicates it to be a mixture of (2S*,3R*)-3-t-butyldiphenylsilyloxy-6-(2'-carboethoxymethylidene)-2-methyl-2-[4'-methyl-5'-(tetrahydropyran-2''-yloxy)-pentyl]-oxepane and (2S*,3R*)-3-t-butyldiphenylsilyloxy-6-(2'-carboethoxymethyl)-2-methyl-[4'-methyl-5'-(tetrahydropyran-2''-yloxy)-pentyl]-6-oxepene: nmr (CDCl3)δ 5.5

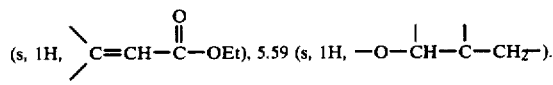

EXAMPLE 7

(2S*,3R*)-3-t-Butyldiphenylsilyloxy-6-(2'-hydroxyethylidene)-2-methyl-2-[4'-methyl-5'-(tetrahydropyran-2''-yloxy)-pentyl]-oxepane (8) and (2S*,3R*)-3-t-butyldiphenylsilyloxy-6-(2'-hydroxyethyl)-2-methyl-2-[4'-methyl-5'-(tetrahydropyran-2''-yloxy)-pentyl]-6-oxepene (9)

A solution of the mixture of (2S*,3R*)-3-t-butyldiphenylsilyloxy-6-(2'-carboethoxymethylidene)-2-methyl-2-[4'-methyl-5'-(tetrahydropyran-2''-yloxy)-pentyl]-oxepane and (2S*,3R*)-3-t-butyldiphenylsilyloxy-6-(2'-carboethoxymethyl)-2-methyl-2-[4'-methyl-5'-(tetrahydropyran-2''-yloxy)-pentyl]-6-oxepene (85 mg, 0.134 mmol) in Et2O (2 ml) is added dropwise to a suspension of lithium aluminum hydride (13 mg, 0.33 mmol) in ether (1 ml) in a nitrogen atmosphere and refluxed for 1 hour. The reaction mixture is then cooled at 25° C. and quenching is accomplished by addition of wet ether (5 ml). The mixture is diluted with saturated ammonium chloride solution and extracted with ether (5×20 ml). The ether phases are combined, dried (MgSO4) and evaporated in vacuo to give 75 mg of a yellow oil. This material is chromatographed on SilicAR CC-7 (1.8 g, Mallinckrodt) in hexane. Elution with 5% ethyl acetate/hexane gives (2S*,3R*)-3-t-butyldiphenylsilyloxy-6-(2'-hydroxyethyl)-2-methyl-2-[4'-methyl-5'-(tetrahydropyran-2''-yloxy)-pentyl]-6-oxepene (33 mg): nmr (CDCl3)δ 1.05 (s, 9H, -t-butyl), 3.45

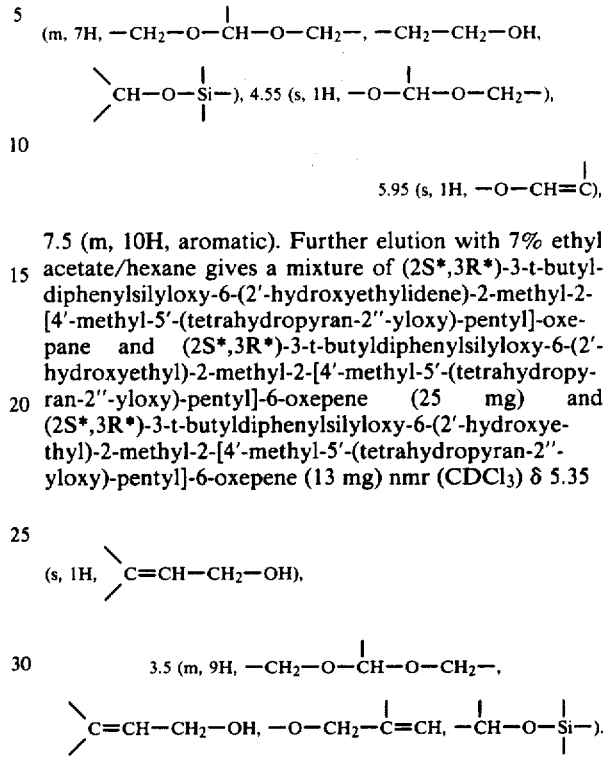

7.5 (m, 10H, aromatic). Further elution with 7% ethyl acetate/hexane gives a mixture of (2S*,3R*)-3-t-butyldiphenylsilyloxy-6-(2'-hydroxyethylidene)-2-methyl-2-[4'-methyl-5'-(tetrahydropyran-2''-yloxy)-pentyl]-oxepane and (2S*,3R*)-3-t-butyldiphenylsilyloxy-6-(2'-hydroxyethyl)-2-methyl-2-[4'-methyl-5'-(tetrahydropyran-2''-yloxy)-pentyl]-6-oxepene (25 mg) and (2S*,3R*)-3-t-butyldiphenylsilyloxy-6-(2'-hydroxyethyl)-2-methyl-2-[4'-methyl-5'-(tetrahydropyran-2''-yloxy)-pentyl]-6-oxepene (13 mg) nmr (CDCl3) δ 5.35

EXAMPLE 8

(2S*,3R*)-3-t-Butyldiphenylsilyloxy-6-(2'-t-butyldiphenylsilyloxyethylidene)-2-methyl-2-[4'-methyl-5'-(tetrahydropyran-2''-yloxy)-pentyl]-oxepane (10)

t-Butyldiphenylsilyl chloride (275 mg, 0.001 mol) in dimethylformamide (1 ml) and imidazole (68 mg, 0.001 mol) are added to a solution of (2S*,3R*)-3-t-butyldiphenylsilyloxy-6-(2'-hydroxyethylidene)-2-methyl-[4'-methyl-5'-(tetrahydropyran-2''-yloxy)-pentyl]-oxepane (275 mg, 0.001 mol) in dimethylformamide (3 ml) at 23° C. in a nitrogen atmosphere. The mixture is stirred for 18 hours at 23° C. and then poured into a saturated sodium chloride solution (20 ml) and extracted with ether (5×50 ml). The ether phases are combined, dried (MgSO4) and evaporated in vacuo to give 890 mg of a yellow oil. This material is chromatographed on SilicAR CC-7 (5 g, Mallinckrodt) in hexane. Elution with 7.5% ethyl acetate/hexane gives (2S*,3R*)-3-t-butyldiphenylsilyloxy-6-(2'-t-butyldiphenylsilyloxyethylidene)-2-methyl-2-[4'-methyl-5'-(tetrahydropyran-2''-yloxy)-pentyl]-oxepane as a light yellow oil.

EXAMPLE 9

(2S*,3R*)-3-t-Butyldiphenylsilyloxy-6-(2''-t-butyldiphenylsilyloxyethylidene)-2methyl-2-(4'-methyl-5'-hydroxypentyl)oxepane (11)

A solution of (2S*,3R*)-3-t-butyldiphenylsilyloxy-6-(2'-t-butyldiphenylsilyloxyethylidene)2-methyl-2-[4'-methyl-5'-(tetrahydropyran-2''-yloxy)-pentyl-oxepane (832 mg, 0.001 mole), methanol (4 ml) and acetic acid (4 ml) is heated to 40° C. and stirred and maintained at this temperature for 18 hours under a nitrogen atmosphere. The reaction mixture is cooled and the methanol and acetic acid are evaporated under reduced pressure. The mixture is diluted with water (10 ml) and the aqueous layer is extracted with ether (3×50 ml). The combined organic layers are washed with saturated sodium bicarbonate, water and saturated sodium chloride and dried (MgSO$_4$). The solvents are removed under reduced pressure and the crude product (780 mg) is chromatographed on SilicAR CC-7 (9 g, Mallinckrodt) in hexane. Elution with 15% ethyl acetate/hexane gives (2S*,3R*)-3-t-butyldiphenylsilyloxy-6-(2''-t-butyldiphenylsilyloxyethylidene)-2-methyl-2-(4'-methyl-5'-hydroxypentyl)-oxepane as a colorless oil.

EXAMPLE 10

(2S*,3R*)-3-Butyldiphenylsilyloxy-6-(2''-t-butyldiphenylsilyloxyethylidene)-2-methyl-2-(4'-methyl-5'-oxopentyl)-oxepane (12)

A pyridine chromium trioxide solution [pyridine (0.96 g, 0.012 mol) and chromium trioxide (0.600 g, 0.006 mole)] is prepared in dry methylene chloride (20 ml) at 0° C. in a nitrogen atmosphere. The cooling bath is removed and celite (3 g) is added at 15° C. The solution is cooled to 0° C. and treated with (2S*,3R*)-3-t-butyldiphenylsilyloxy-6-(2''-t-butyldiphenylsilyloxyethylidene)-2-methyl-2-(4'-methyl-5'-hydroxypentyl)oxepane (0.743 g, 0.001 mole) in methylene chloride (5 ml). After 1 hour the mixture is filtered and the celite cake is washed with methylene chloride (10×10 ml). The organic phases are combined, washed with saturated sodium bicarbonate (2×50 ml), saturated sodium chloride and dried (MgSO$_4$). The solvent is removed at reduced pressure and the resulting crude product is chromatographed on SilicAR CC-7 (10 g, Mallinckrodt). Elution with 15-20% ethyl acetate/hexane gives (2S*,3R*)-3-t-butyldiphenylsilyloxy-6-(2'-t-butyldiphenylsilyloxyethylidene)-2-methyl-2-(4'-methyl-5'-oxopentyl)-oxepane as a yellowish oil.

EXAMPLE 11

(2S*,3R*)-3-t-Butyldiphenylsilyloxy-6-(2''-t-butyldiphenylsilyloxyethylidene)-2-(4',8'-dimethyl-5'-hydroxy-6'-nonynyl)-2-methyloxepane (13)

A solution of ethyl bromide (229 mg, 2.1 mmol) in anhydrous tetrahydrofuran (3 ml) is added over 15 minutes to a suspension of magnesium turnings (50 mg, 2 mmoles) in tetrahydrofuran (3 ml). After the magnesium has dissolved, the solution is cooled to 0° C. and a solution of 3-methyl-1-butyne (142 mg, 2.1 mmol) in anhydrous tetrahydrofuran (5 ml) is added over a period of 5 minutes. This solution is added dropwise via cannula over 10 minutes to a solution of (2S*,3R*)-3-t-butyldiphenylsilyloxy-6-(2''-t-butyldiphenylsilyloxyethylidene)-2-methyl-2-(4'-methyl-5'-oxopentyl)-oxepane (0.700 g, 1 mmole) in tetrahydrofuran (4 ml). The mixture is stirred for 0.5 hours, quenched with water (10 ml), poured into water, saturated sodium chloride, dried (MgSO$_4$) and evaporated in vacuo to give 800 mg of a yellow oil. The oil is chromatographed on SilicAR CC-7 (4 g, Mallinckrodt) in hexane. Elution with 7-10% ethyl acetate/hexane gives (2S*,3R*)-3-t-butyldiphenylsilyloxy-6-(2''-t-butyldiphenylsilyloxyethylidene)-2-(4',8'-dimethyl-5'-hydroxy-6'-nonynyl)-2-methyloxepane as a colorless oil.

EXAMPLE 12

(2S*,3R*)-3-t-Butyldiphenylsilyloxy-6-(2''-t-butyldiphenylsilyloxyethylidene)-2-(4',8'-dimethyl-5'-hydroxy-6'-nonenyl)-2-methyloxepane (14)

A solution of (2S*,3R*)-3-t-butyldiphenylsilyloxy-6-(2''-t-butyldiphenylsilyloxyethylidene)-2-(4',8'-dimethyl-5'-hydroxy-6'-nonynyl)-2-methyloxepane (0.81 g, 0.001 mol) in anhydrous tetrahydrofuran (5 ml) is added dropwise to a suspension of lithium aluminum hydride (76.5 mg, 0.002 mol) in anhydrous tetrahydrofuran (5 ml) under nitrogen. The mixture is refluxed for 3 hours and then stirred at room temperature for 18 hours. Quenching is accomplished by the successive addition of water (0.3 ml), 15% aqueous sodium hydroxide (0.3 ml) and water (0.9 ml). The mixture is filtered and the solids are washed with ether. The organic layer is washed with water, saturated sodium chloride, dried (MgSO$_4$) and evaporated to give 790 mg of a clear colorless oil. The oil is chromatographed on SilicAR CC-7 (10 g, Mallinckrodt). Elution with 10% ethyl acetate/hexane gives (2S*,3R*)-3-t-butyldiphenylsilyloxy-6-(2''-t-butyldiphenylsilyloxyethylidene)-2-(4',8'-dimethyl-5'-hydroxy-6'-nonenyl)-2-methyloxepane as a colorless oil.

EXAMPLE 13

(2S*,3R*)-3-t-Butyldiphenylsilyloxy-6-(2''-t-butyldiphenylsilyloxyethylidene)-2-(4',8'-dimethyl-6'-nonenyl-5'-oxo)-2-methyloxepane (15)

Chromium trioxide (0.600 g, 0.006 mole) is added to a solution of pyridine (0.96 g, 0.012 mol) in anhydrous methylene chloride (20 ml) of 0° C. under nitrogen. The mixture is allowed to warm to room temperature and celite (3 g) is added. The solution is cooled to 0° C. and (2S*,3R*)-3-t-butyldiphenylsilyloxy-6-(2''-t-butyldiphenylsilyloxyethylidene)-2-(4',8'-dimethyl-5'-hydroxy-6'-nonenyl)-2-methyloxepane (0.810 mg, 0.001 mole) in methylene chloride (10 ml) is added. After 1 hour, the mixture is filtered and the solids are washed with methylene chloride. The organic phases are combined, washed with saturated sodium bicarbonate (2×50 m), saturated copper sulfate, water, saturated sodium chloride and dried (MgSO$_4$). The solvent is removed at reduced pressure and the resulting crude product (700 mg) is chromatographed on SilicAR CC-7 (10 g, Mallinckrodt). Elution with 10-22% ethyl acetate/hexane gives (2S*,3R*)-3-t-butyldiphenylsilyloxy-6-(2''-t-butyldiphenylsilyloxyethylidene)-2-(4',8'-dimethyl-6'-nonenyl-5'-oxo)-2-methyloxepane as a colorless oil.

EXAMPLE 14

(2S*,3R*)-3-t-Butyldiphenylsilyloxy-6-(2''-t-butyldiphenylsilyloxyethylidene)-2-(4',8'-dimethyl-7'-nonenyl-5'-oxo)-2-methyloxepane (16)

A solution of (2S*,3R*)-3-t-butyldiphenylsilyloxy-6-(2''-butyldiphenylsilyloxyethylidene)-2-(4',8'-dimethyl-6'-nonenyl-5'-oxo)-2-methyloxepane (179 mg, 0.22×10$^{-3}$ mole) in tertiary butanol (3 ml) is added to a solution of potassium t-butoxide [K(87 mg, 2.21×10$^{-3}$ mole) and t-BuOH (7 ml)] in a nitrogen atmosphere. The solution is stirred for 16 hours and quenched with 10% acetic acid (10 ml). The solution is then poured into saturated sodium bicarbonate (50 ml) and extracted with ether (5×25 ml). The ether phases are combined, washed with water (2×25) and saturated sodium chloride (25 ml), dried (MgSO₄) and the ether is removed under reduced pressure to give (2S*,3R*)-3-t-butyldiphenylsilyloxy-6-(2″-t-butyldiphenylsilyloxyethylidene)-2-(4′,8′-dimethyl-7′-nonenyl-5′-oxo-2-methyloxepane as a light yellow oil.

EXAMPLE 15

(2S*,3R*)-3-t-Butyldiphenylsilyloxy-6-(2″-t-butyldiphenylsilyloxyethylidene)-2-(4′,8′-dimethyl-5′-hydroxy-7-nonenyl)-2-methyloxepane (17)

To a solution of (2S*,3R*)-3-t-butyldiphenylsilyloxy-6-(2″-t-butyldiphenylsilyloxyethylidene)-2-(4′,8′-dimethyl-7′-nonenyl-5′-oxo)-2-methyloxepane (0.804 g, 0.001 mol) in absolute EtOH (20 ml) at 0° C. is added a solution of sodium borohydride (38 mg, 0.001 mol) in absolute EtOH (10 ml) over a period of 30 minutes. The resulting yellow solution is stirred at 0° C. for 5 hours. The ethanol is removed by distillation at reduced pressure, the residue is poured into saturated sodium chloride solution (25 ml) and the product is extracted with chloroform (3×50 ml). The organic layers are combined, dried (MgSO₄) and evaporated in vacuo. The crude product is chromatographed on SilicAR CC-7 (10 g, Mallinckrodt). Elution with 15% ethyl acetate/hexane gives (2S*,3R*)-3-t-butyldiphenylsilyloxy-6-(2″-t-butyldiphenylsilyloxyethylidene)-2-(4′,8′-dimethyl-5′-hydroxy-7-nonenyl)-2-methyloxepane (790 mg, 95%) as a colorless oil.

EXAMPLE 16

(2S*,3R*)-3-t-Butyldiphenylsilyloxy-6-(2″-t-butyldiphenylsilyloxyethylidene)-2-[4′,8′-dimethyl-5′-(tetrahydropyran-2″-yloxy)-7-nonenyl]-2-methyloxepane (18)

A mixture of the alcohol (2S*,3R*)-3-t-butyldiphenylsilyloxy-6-(2″-t-butyldiphenylsilyloxyethylidene)-2-(4′,8′-dimethyl-5′-hydroxy-7-nonenyl)-2-methyloxepane (0.806 g, 0.001 mol), dihydropyran (168 mg, 0.002 mol) and p-toluenesulfonic acid (25 mg) in anhydrous ether (10 ml) is stirred at 23° C. under a nitrogen atmosphere for 18 hours. The mixture is diluted with ether (100 ml), washed with saturated sodium bicarbonate, water, and saturated sodium chloride, dried (MgSO₄) and evaporated under reduced pressure to give the crude product. The crude product is chromatographed on SilicAR CC-7 (5 g, Mallinckrodt). in hexane. Elution with ethyl acetate/hexane gives (2S*,3R*)-3-t-butyldiphenylsilyloxy-6-(2″-t-butyldiphenylsilyloxyethylidene)-2-[4′,8′-dimethyl-5′-(tetrahydropyran-2″-yloxy)-7-nonenyl]-2-methyloxepane as a colorless oil (0.880 g, 98%).

EXAMPLE 17

(2S*,3R*)-6Z-(2″-Hydroxyethylidene)-2-methyl-2-[4′,8′-dimethyl-5′-(tetrahydropyran-2″-yloxy)-7′-nonenyl)-oxepan-3-ol (19) and
(2S*,3R*)-6E-(2″-Hydroxyethylidene)-2-methyl-2-[4′,8′-dimethyl-5′-(tetrahydropyran-2″-yloxy)-7′-nonenyl]-oxepan-3-ol (20)

Compound (2S*,3R*)-3-t-butyldiphenylsilyloxy-6-(2″-t-butyldiphenylsilyoxyethylidene)-2-[4′,8′-dimethyl-5′-(tetrahydropyran-2″-yloxy)-7-nonenyl]-2-methyloxepane (0.890 g, 0.001 mol) is dissolved in tetrahydrofuran (20 ml) under nitrogen and treated with 0.8 M tetrabutylammonium fluoride in tetrahydrofuran (30 ml). The solution is stirred for 2 hours. The solvent is evaporated under reduced pressure, diluted with water (20 ml) and the aqueous layer extracted with ether (5×100 ml). The organic layers are combined, washed with saturated sodium chloride (25 ml), dried (MgSO₄) and evaporated in vacuo to give a slightly yellow oil (0.590 g). The material is chromatographed on silica gel (16 g, Baker) in hexane. Elution with 22% to 24% ethyl acetate/hexane gives (2S*,3R*)-6Z-(2″-hydroxyethylidene)-2-methyl-2-[4′,8′-dimethyl-5′-(tetrahydropyran-2″-yloxy)-7′-nonenyl]-oxepan-3-ol (155 mg): nmr (CDCl₃)δ 0.85 (d, 3H, J=6 Hz, -CH-CH₃), 1.18 (s, 3H, CH₃), 2.2

(m, 4H, —CH₂—CH₂—C=CH and

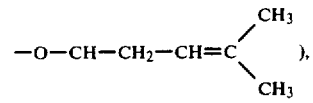), 4.2 (m, 4H, —O—CH₂—CH—C=CH, and

—C=CH—CH₂OH), 4.68 (broad s, 1H, —CH—O—CH—O—), 5.32 (m, 2H, —C=CH₂OH and 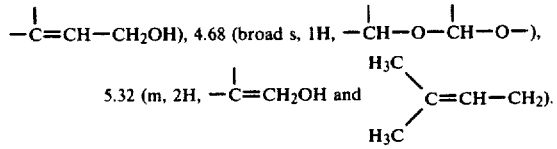

Further elution with 24% to 26% ethyl acetate gives (2S*,3R*)-6E-(2″-hydroxyethylidene)-2-methyl-[4′,8′-dimethyl-5′-(tetrahydropyran-2″-yloxy)-7′-nonenyl]-oxepan-3-ol (222 mg), nmr (CDCl₃)δ 0.9

(d, 3H, J=6 Hz, —CH—CH₃), 1.15 (s, 3H, CH₃), 4.18 (m, 4H,

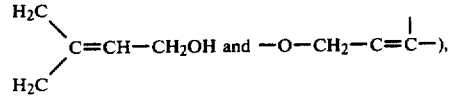 C=CH—CH₂OH and —O—CH₂—C=C—), 4.65 (broad s, 1H, —CH—O—CH—O—), 5.30 (m, 2H, —C=CH—CH₂OH and 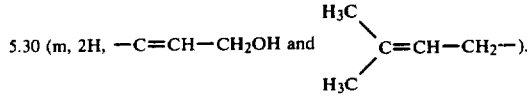

EXAMPLE 18

(2S*,3R*)-3-Acetoxy-6Z-(2″-acetoxyethylidene)-2-methyl-2-[4′,8′-dimethyl-5′-(tetrahydropyran-2′-yloxy)-7′-nonenyl]oxepane (21)

A solution of (2S*,3R*)-6Z-(2″-hydroxyethylidene)-2-methyl-2-[4′,8′-dimethyl-5′-(tetrahydropyran-2″-yloxy)-7′-nonenyl]-oxepan-3-ol (0.172 g, 0.00040 mole) in pyridine (2 ml) and acetic anhydride (0.2 ml) is stirred under nitrogen at 24° C. for 18 hours. The reaction mixture is then poured into water and stirred for 1.5 hours. The suspension is extracted with ether (5×50 ml) and the ether extracts washed with water, saturated copper sulfate solution, dried (MgSO₄) and evaporated in vacuo to give 170 mg of a yellowish oil. The oil is chromatographed on silica gel (2 g, Baker) in hexane. Elution with 10% ethyl acetate/hexane gives (2S*,3R*)-3-acetoxy-6Z-(2″-acetoxyethylidene)-2- methyl-2-[4',8'-dimethyl-5'-(tetrahydropyran-2"-yloxy)-7'-nonenyl]-oxepane (166 mg, 82%): nmr (CDCl$_3$)δ 0.9

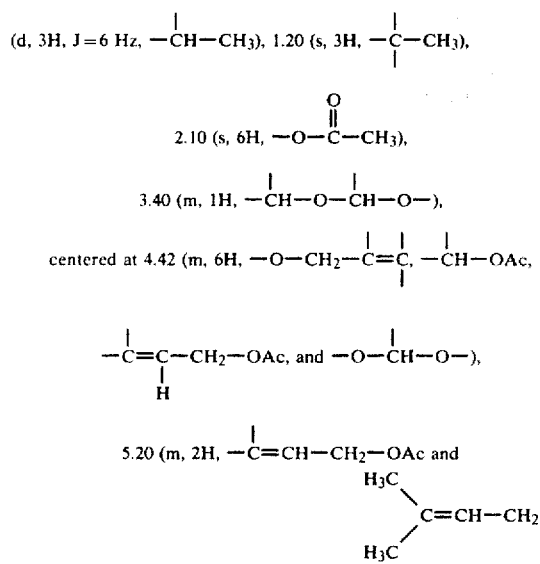

EXAMPLE 19

(2S*,3R*)-3-Acetoxy-6Z-(2"-acetoxyethylidene)-2-methyl-2-[4',8'-dimethyl-5'-hydroxy-7'-nonenyl]-oxepane (22)

A solution of (2S*,3R*)-3-acetoxy-6Z-(2"-acetoxyethylidene)-2-methyl-2-[4',8'-dimethyl-5'-(tetrahydropyran-2"-yloxy)-7'-nonenyl]-oxepane (80 mg, 0.000157 moles) in acetic acid/water/tetrahydrofuran 20:10:1 (3 ml) is stirred under nitrogen at 40° C. for 4 hours. The reaction mixture is cooled and poured into ether (50 ml) and the ether washed with saturated bicarbonate (50 ml). The ether phase is separated and the aqueous phase is extracted with ether (3×25 ml). The ether phases are combined and dried (MgSO$_4$). The solvents are removed under reduced pressure and the crude product (72 mg) is chromatographed on silica gel (1.1 g, Baker) in hexane. Elution with 8% ethyl acetate/hexane gives (2S*,3R*)-3-acetoxy-6Z-(2"-acetoxyethylidene)-2-methyl-2-[4',8'-dimethyl-5-hydroxy-7'-nonenyl]-oxepane (61 mg, 90%): ir (neat) 3400 (OH), 1724 cm$^{-1}$ (OAc); nmr (CDCl$_3$)δ 0.90

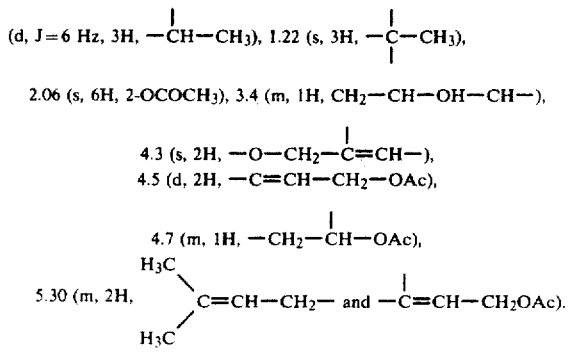

EXAMPLE 20

(2S*,3R*)-3-Acetoxy-6Z-(2"-acetoxyethylidene)-2-methyl-2-[4',8'-dimethyl-7'-nonenyl-5'-oxo]-oxepane (23)

A pyridine-chromium trioxide solution [pyridine (345 mg, 0.00385 mole) and chromium trioxide (192 mg, 0.00192 mole)] is prepared in dry methylene chloride (27 ml) at 0° C. in a nitrogen atmosphere. The cooling bath is removed and celite (1.5 g) is added at 10° C. The solution is cooled to 0° C. and (2S*,3R*)-3-acetoxy-6Z-(2"-acetoxyethylidene)-2-methyl-2-[4',8'-dimethyl-5'-hydroxy-7'-nonenyl]-oxepane (136 mg, 0.00032 mole) is added. After 1 hour, the mixture is filtered and the celite cake is washed with methylene chloride (10×10 ml). The organic phases are combined, washed with saturated sodium bicarbonate (2×25 ml), saturated sodium chloride and dried (MgSO$_4$). The solvent is removed at reduced pressure and the resulting crude product (140 mg) is chromatographed on silica gel (1.5 g, Baker) in hexane. Elution with 8% ethyl acetate/hexane gives a colorless oil (2S*,3R*)-3-acetoxy-6Z-(2"-acetoxyethylidene)-2-methyl-2-[4',8'-dimethyl-7'-nonenyl-5'-oxo]-oxepane (57) (100 mg, 84%): ir (neat) 1740 (OAc), 1710 cm$^{-1}$ (CO), nmr (CDCl$_3$)δ1.10

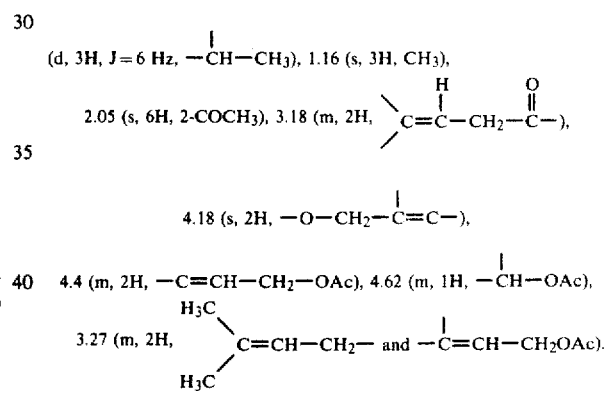

EXAMPLE 21

(2S*,3R*)-3-Acetoxy-6E-(2"-acetoxyethylidene)-2-methyl-2-[4',8'-dimethyl-5'-(tetrahydropyran-2"-yloxy)-7'-nonenyl)-oxepane (25)

A solution of (2S*,3R*)-6E-(2"-hydroxyethylidene)-2-methyl-2-[4',8'-dimethyl-5'-(tetrahydropyran-2"-yloxy)-7'-nonenyl]-oxepan-3-ol (252 mg, 0.000594 mole) in pyridine (3 ml) and acetic anhydride (0.3 ml) is stirred under nitrogen at 24° C. for 18 hours. The reaction mixture is then poured into water and stirred for 1.5 hours. The suspension is extracted with ether (5×50 ml) and the ether extracts are washed with water, saturated copper sulfate solution, dried (MgSO$_4$) and evaporated in vacuo to give a yellowish oil (300 mg). The oil is chromatographed on silica gel (3 g, Baker) in hexane. Elution with 10% ethyl acetate/hexane gives (2S*,3R*)-3-acetoxy-6E-(2"-acetoxyethylidene)-2-methyl-2-[4',8'-dimethyl-5'-(tetrahydropyran-2"-yloxy)-7'-nonenyl]-oxepane (283 mg, 96%): nmr (CDCl$_3$)δ0.80 (d, J=6 Hz, 3H, -CH-C$\underline{H}_3$), 0.90

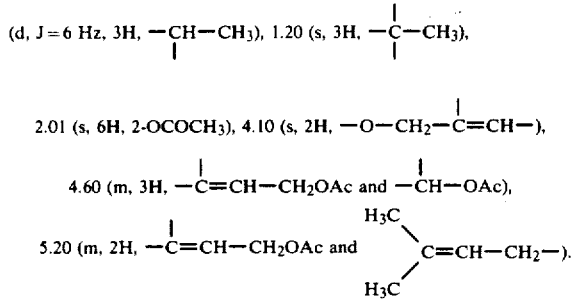

EXAMPLE 22

(2S*,3R*)-3-Acetoxy-6E-(2''-acetoxyethylidene)-2-methyl-2-[4',8'-dimethyl-5'-hydroxy-7'-nonenyl]-oxepane (26)

A solution of (2S*,3R*)-3-acetoxy-6E-(2''-acetoxyethylidene)-2-methyl-2-[4',8'-dimethyl-5'-(tetrahydropyran-2''-yloxy)-7'-nonenyl]-oxepane (280 mg, 0.00055 mole), in acetic acid/water/tetrahydrofuran 20:10:1 (5 ml) is stirred under nitrogen at 40° C. for 4 hours. The reaction mixture is cooled and poured into ether (50 ml) and the ether mixture is washed with saturated sodium bicarbonate (50 ml). The ether phase is separated and the aqueous phase is extracted with ether (4×50 ml). The ether phases are combined and dried (MgSO₄). The solvents are removed under reduced pressure and the crude product (230 mg) is chromatographed on silica gel (2.3 g, Baker) in hexane. Elution with 8% ethyl acetate/hexane gives (2S*,3R*)-3-acetoxy-6E-(2''-acetoxyethylidene)-2-methyl-2-[4',8'-dimethyl-5'-hydroxy-7'-nonenyl]-oxepane (196 mg, 84%): nmr (CDCl₃)δ0.90

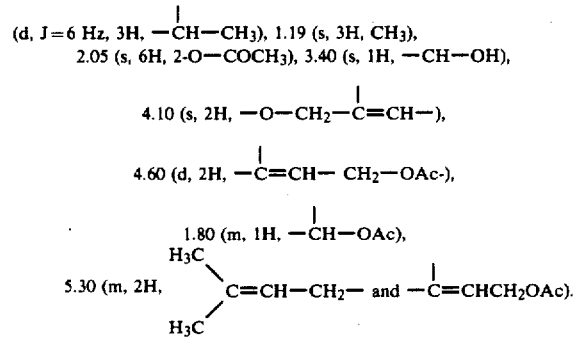

EXAMPLE 23

(2S*,3R*)-3-Acetoxy-6E-(2''-acetoxyethylidene)-2-methyl-2-[4',8'-dimethyl-7'-nonenyl-5'-oxo]-oxepane (27)

A solution of pyridine (440 mg, 0.00558 mole) and chromium trioxide (279 mg, 0.00279 mole) in methylene chloride (25 ml) in a nitrogen atmosphere is stirred for 45 minutes at 0° C. Celite (2 g) is added followed by (2S*,3R*)-3-acetoxy-6-E-(2''-acetoxyethylidene)-2-methyl-2-[4',8'-dimethyl-5'-hydroxy-7'-nonenyl]-oxepane (197 mg, 0.000465 mole) in methylene chloride (25 ml). The mixture is stirred for 90 minutes at 23° C. The mixture is then filtered and the celite cake is washed with methylene chloride (10×10 ml). The filtrate and the washings are combined and the methylene chloride extracts are washed with sodium bicarbonate, water and saturated sodium chloride, dried (MgSO₄) and evaporated in vacuo. The crude product (201 mg) is chromatographed on silica gel (3 g, Baker) in hexane. Elution with 8% ethyl acetate/hexane gives (2S*,3R*)-3-acetoxy-6E-(2''-acetoxyethylidene)-2-methyl-2-[4',8'-dimethyl-7'-nonenyl-5'-oxo]-oxepane as a colorless oil (173 mg, 88%): ir (neat) 1710 (CO), 1740 (OAc) cm⁻¹, nmr (CDCl₃)δ1.0 (d, 3H, J=6 Hz, -CHCH₃), 1.18

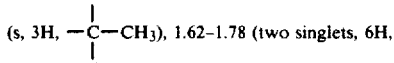

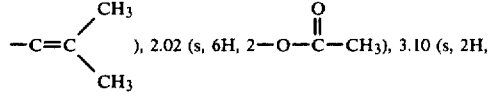

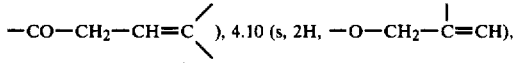

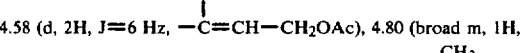

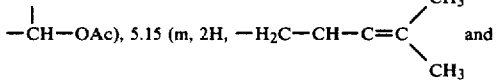

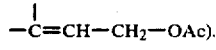

EXAMPLE 24

(2S*,3R*)-6E-(2''-Hydroxyethylidene)-2-methyl-2-[4',8'-dimethyl-5'-oxo-7'-nonenyl]-oxepan-3-ol (28)

A solution of (2S*,3R*)-3-acetoxy-6E-(2''-acetoxyethylidene)-2-methyl-2-[4',8'-dimethyl-7'-nonenyl-5'-oxo)-oxepane (173 mg, 0.000410 mole), tetrabutylammonium hydroxide in methanol (40% solution, 1 ml), water (4 ml) and tetrahydrofuran (4 ml) at 25° C. in a nitrogen atmosphere is stirred for 24 hours. The solution is then diluted with saturated sodium chloride (50 ml) and the aqueous layer is extracted with ethyl acetate (5×50 ml). The combined organic layers are dried (MgSO₄) and evaporated in vacuo. The crude product (170 mg) is chromatographed on silica gel (3.5 g, Baker) in chloroform. Elution with chloroform gives (2S*,3R*)-6E-(2''-hydroxyethylidene)-2-methyl-2-[4',8'-dimethyl-5'-oxo-7'-nonenyl]-oxepan-3-ol as a colorless oil (110 mg, 80%): ir (neat) 3448 (OH) 1709 (CO) cm⁻¹, 5.41

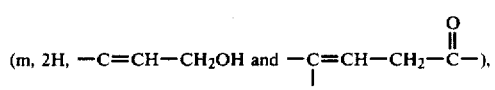

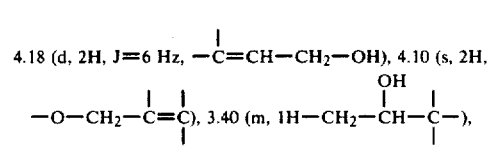

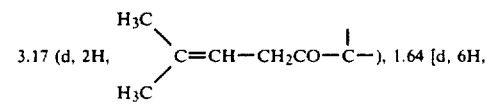

—HC=C—(CH₃)₂], 1.18 (s, 3H, 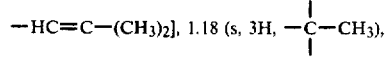

1.05 (d, J=6 Hz, 3H, -CH=CH₃); Mass spectrum m/e, 320 (M-18), 302 (M-2H₂O), 251, 233, 141, 125, 113, 97, 95, 81, 69.

EXAMPLE 25

(2S*,3R*)-6Z-(2''-Hydroxyethylidene)-2-methyl-2-[4',8'-dimethyl-5'-oxo-7'-nonenyl]-oxepan-3-ol (24)

A solution of (2S*,3R*)-3-acetoxy-6Z-(2''-acetoxyethylidene)-2-methyl-2-[4',8'-dimethyl-7'-nonenyl-5'-oxo]-oxepane (100 mg, 0.000236 mole), tetrabutylammonium hydroxide in methanol (40% solution, 1 ml), water (4 ml) and tetrahydrofuran (4 ml) at 25° C. in a nitrogen atmosphere is stirred for 24 hours. The solution is diluted with saturated sodium chloride (50 ml) and the aqueous layer is extracted with ethyl acetate (5×50 ml). The combined organic layers are dried (MgSO₄) and evaporated in vacuo. The crude product (210 mg) is chromatographed on silica gel (1.5 g, Baker) in chloroform. Elution with chloroform gives (2S*,3R*)-6Z-(2''-hydroxyethylidene)-2-methyl-2-[4',8'-dimethyl-5'-oxo-7'-nonenyl]-oxepan-3-ol as a colorless oil (65 mg, 81%): ir (neat) 3448 (OH), 1709 (CO) cm⁻¹, nmr (CDCl₃)δ5.41

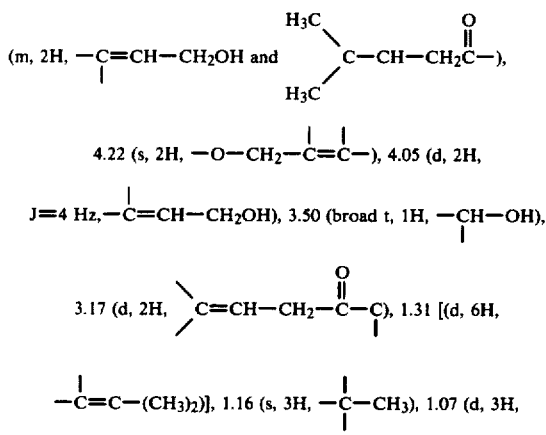

4.22 (s, 2H, —O—CH₂—C=C—), 4.05 (d, 2H,

J=4 Hz,—C=CH—CH₂OH), 3.50 (broad t, 1H, —CH—OH), 3.17 (d, 2H, \C=CH—CH₂—C—C), 1.31 [(d, 6H, —C=C—(CH₃)₂)], 1.16 (s, 3H, —C—CH₃), 1.07 (d, 3H, J=6 Hz, —CH—CH₃);
m/e, 320 (M-18), 302 (M -2H₂O), 251, 233, 141, 125, 113, 97, 95, 81, 69.

Preparation of starting material:

EXAMPLE A (1R*,9R*)-1-Acetoxy-6,6-ethylenedioxy-9-methyl-4(10)-octalin

A mixture of (1R*,9R*)-1-acetoxy-9-methyl-5(10)-octalin-6-one (23 g, 0.103 mol), ethylene glycol (100 ml) and p-toluenesulfonic acid (100 mg) in benzene (700 ml) is refluxed for 16 hours using a Dean-Stark apparatus. The cooled solution is diluted with water (500 ml) and ether (500 ml). The organic layer is separated and the aqueous layer is extracted with ether (2×250 ml). The combined organic layers are washed with saturated sodium bicarbonate (4×200 ml), water (2×200 ml) and saturated sodium chloride, and dried (MgSO₄). The solvents are removed at reduced pressure and the crude product (26 g) is chromatographed on SilicAR CC-7 (350 g, Mallinckrodt) in hexane. Elution with 7–10% ethyl acetate/hexane gives (1R*,9R*)-1-acetoxy-6,6-ethylenedioxy-9-methyl-4(10)-octalin as a colorless oil (22 g, 80%): ir (neat) 1724 cm⁻¹ (OAc); nmr (CDCl₃)δ1.19 (s, 3H, CH₃), 2.02 (s, 3H, -OCO-CH₃), 3.98 (s, 4H, ketal), 4.82

(m, 1H, —CH—OAc), 5.35 (m, 1H, —C=CH—).

EXAMPLE B (1R*,9R*)-6,6-Ethylenedioxy-1-hydroxy-9-methyl-4(10)-octalin

A solution of (1R*,9R*)-1-acetoxy-6,6-ethylenedioxy-9-methyl-4(10)-octalin (22 g, 0.0827 mol) and saturated potassium carbonate (100 ml) in methanol (800 ml) and water (100 ml) at 25° C. in a nitrogen atmosphere is stirred for 48 hours. The methanol is evaporated under reduced pressure, diluted with water (500 ml) and the aqueous layer is extracted with chloroform (2×700 ml). The combined organic layers are washed with water (3×600 ml) and saturated sodium chloride (3×700 ml), dried (MgSO₄) and evaporated in vacuo. The crude product (19 g) is chromatographed on SilicAR CC-7 (234 g, Mallinckrodt) in hexane. Elution with 20% ethyl acetate/hexane gives (1R*,9R*)-ethylenedioxy-1-hydroxy-9-methyl-4(10)-octalin as a colorless oil (16.6 g, 87%): ir (KBr) 3546 cm⁻¹ (OH): nmr (CDCl₃)δ1.10 (s, 3H, CH₃), 3.60

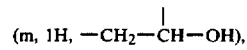
(m, 1H, —CH₂—CH—OH), 3.98 (s, 4H, ketal), 5.27

(m, 1H, —C=CH—CH₂—).

EXAMPLE C (1R*,9R*)-1-Benzyloxy-6,6-ethylenedioxy-9-methyl-4(10)-octalin

To a suspension of sodium hydride (18.7 g, 0.780 mol, 50% dispersion in oil, previously washed with hexane) in benzene (1200 ml) is added the alcohol (1R*,9R*)-6,6-ethylenedioxy-1-hydroxy-9-methyl-4(10)-octalin (87.37 g, 0.390 mol) in benzene (100 ml) in a nitrogen atmosphere. After 0.5 hours, benzylbromide (115.0 g, 0.672 mol) in benzene (100 ml) is added. The mixture is refluxed for 24 hours, cooled and poured into saturated sodium chloride (1000 ml). The aqueous layer is extracted with diethyl ether (3×250 ml). The organic phases are combined, dried (MgSO₄) and the solvents are removed under reduced pressure. The crude product (137.1 g) is chromatographed on SilicAR CC-7 (550 g, Mallinckrodt) in hexane. Elution with 5–10% ethyl acetate/hexane gives (1R*,9R*)-1-benzyloxy-6,6-ethylenedioxy-9-methyl-4(10)-octalin as a clear colorless oil (111.7 g, 91%); nmr (CDCl₃)δ1.20 (s, 3H, CH₃), 3.36

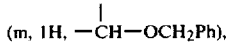

3.98 (s, 4H, ketal), 4.56 (d of d, J=10 Hz, 2H, Ph-C$\underline{H}_2$-O-), 5.23

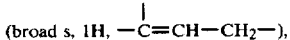

7.23 (s, 5H, aromatic).

EXAMPLE D (1R*,9R*)-1-Benzyloxy-9-methyl-5(10)-octalin-6-one

A mixture of (1R*,9R*)-1-benzyloxy-6,6-ethylenedioxy-9-methyl-4(10)-octalin (111.7 g, 0.355 mol), methanol (400 ml) and acetic acid (400 ml) is refluxed for 18 hours under a nitrogen atmosphere. The reaction mixture is cooled and the methanol and acetic acid evaporated under reduced pressure. The mixture is diluted with water (800 ml) and the aqueous layer extracted with ether (3×1000 ml). The combined organic layers are washed with saturated sodium bicarbonate, water and saturated sodium chloride and dried (MgSO$_4$). The solvents are removed under reduced pressure and the crude product (94.2 g) is chromatographed on SilicAR CC-7 (900 g, Mallinckrodt) in hexane. Elution with 10% ethyl acetate/hexane gives (1R*,9R*)-1-benzyloxy-9-methyl-5(10)-octalin-6-one as a colorless oil (85.4 g, 89%): ir (neat) 1660, 1612 cm$^{-1}$ ($\alpha,\beta$-unsaturated CO); nmr (CDCl$_3$)$\delta$1.22 (s, 3H, C$\underline{H}_3$), 3.16 (m, 1H, -CH-OC$\underline{H}_2$Ph), 4.56 (d of d, J=10 Hz, 2H, Ph-C$\underline{H}_2$-O-), 5.78

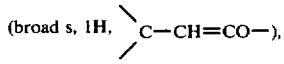

7.30 (s, 5H, aromatic).

EXAMPLE E (1R*,9R*)-1-Benzyloxy-9-methyl-5(10)-oxido-octalin-6-one

To a solution of (1R*,9R*)-1-benzyloxy-9-methyl-5(10)-octalin-6-one (81.2 g, 0.300 mol) in methanol (600 g) cooled to 0° C. under nitrogen is added with stirring 30% hydrogen peroxide (136 g, 1.2 mol). While maintaining the temperature at 0° C., 6 N sodium hydroxide (30 ml) is added dropwise over 20 minutes. After the addition is complete, the reaction mixture is stirred for 4 hours at 25° C. The reaction mixture is then poured into saturated sodium chloride (2000 ml) and extracted with diethyl ether (7×1000 ml). The combined organic layers are washed with water and dried (MgSO$_4$). The solvents are removed under reduced pressure to give a mixture of epoxides (1R*,9R*)-1-benzyloxy-9-methyl-5(10)oxido-octalin-6-one (60 g, 70%): ir (neat) 1724 cm$^{-1}$ (CO); nmr (CDCl$_3$)$\delta$1.08 (s, 3H, C$\underline{H}_3$), 1.18 (s, 3H, C$\underline{H}_3$), 2.82 (s, 1H, -CO-CH-CO-), 3.00

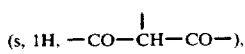

4.4 (d of d, J=10 Hz, 2H, Ph-C$\underline{H}_2$O-), 7.20 (s, 5H, aromatic).

EXAMPLE F (2R*,3R*)-3-Benzyloxy-2-(3'-butynyl)-2-methylcyclohexanone

To a stirred solution of (1R*,9R*)-1-benzyloxy-9-methyl-5(10)-oxido-octalin-6-one (27.8 g, 0.0965 mol) in methylene chloride (500 ml) and acetic acid (350 ml) at 0° C. under nitrogen is added p-toluenesulfonylhydrazide (18.2 g, 0.097 mol) in one portion. Stirring is continued at 0° C. for 3 hours followed by 19 hours at 25° C. The reaction mixture is poured into water (1000 ml) and the methylene chloride layer is separated. The aqueous layer is extracted with methylene chloride (2×500 ml). The combined organic layers are washed with water, saturated sodium bicarbonate (2×750 ml), water, saturated sodium chloride and dried (MgSO$_4$). The solvents are removed at reduced pressure to give a slightly yellow oil (27.5 g, 100%). The crude product is chromatographed on SilicAR CC-7 (600 g, Mallinckrodt) in hexane. Elution with 10% ethyl acetate/hexane gives (2R*,3R*)-3-benzyloxy-2-(3'-butynyl)-2-methylcyclohexanone: ir (neat) 2132 (C≡C), 1704 cm$^{-1}$, (CO); nmr (CDCl$_3$)$\delta$1.20 (s, 3H, C$\underline{H}_3$), 2.38 (m, 1H, -C≡C$\underline{H}$), 3.50

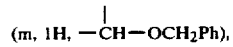

4.56 d of d, J=10 Hz, 2H, Ph-C$\underline{H}_2$-O-), 7.25 (s, 5H, aromatic).

EXAMPLE G (2S*,3R*)-3-Benzyloxy-2-(3'-butynyl)-1,1-ethylenedioxy-2-methylcyclohexane A mixture of (2S*,3R*)-3-benzyloxy-2-(3'-butynyl)-2-methylcyclohexanone (27.5 g, 0.102 mol), ethylene glycol (100 ml) and p-toluenesulfonic acid (1 g) in benzene (600 ml) is refluxed for 20 hours using a Dean-Stark apparatus. The cooled solution is washed with saturated sodium bicarbonate (3×250 ml) and water (2×250 ml) and dried (MgSO$_4$). The solvent is removed at reduced pressure and the crude product (30.3 g) is chromatographed on SilicAR CC-7 (600 g, Mallinckrodt) in hexane. Elution with 3% ethyl acetate/hexane gives (2S*,3R*)-3-benzyloxy-2-(3'-butynyl)-1,1-ethylenedioxy-2-methylcyclohexane as a colorless oil (23.9 g, 75%): ir (neat) 2126 cm$^{-1}$ (C≡C); nmr (CDCl$_3$)$\delta$1.06 (s, 3H, C$\underline{H}_3$), 2.30 (m, 1H, -C≡C$\underline{H}$), 3.41

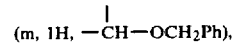

3.98 (s, 4H, ketal), 4.50 (d of d, J=10 Hz, 2H, Ph-C$\underline{H}_2$-O-), 7.20 (s, 5H, aromatic).

EXAMPLE H (2S*,3R*)-3-Benzyloxy-1,1-ethylenedioxy-2-(4'-hydroxy-butyl)-2-methylcyclohexane To a stirred solution of 9-borabicyclononane (37.1 g, 0.304 mol) in dry tetrahydrofuran (1200 ml) maintained at 0° C. in a nitrogen atmosphere is added a solution of (2S*,3R*)-3-benzyloxy-2-(3'-butynyl)-1,1-ethylenedioxy-2-methylcyclohexane (45.2 g, 0.144 mol) in dry tetrahydrofuran (300 ml). After the addition is complete, the mixture is stirred for 5 hours at 25° C. At the end of this period, the reaction mixture is cooled to 0° C. and 3 N sodium hydroxide (140 ml, 0.42 mol) followed by 30% hydrogen peroxide (159.6 g, 1.4 mol) are added while maintaining the temperature at 0° C. After the addition is complete, the mixture is stirred for 1 hour at 25° C. The mixture is then diluted with saturated sodium chloride (2000 ml) and extracted with ether (6×100 ml). The ether phases are combined, dried (MgSO4) and the solvents are removed under reduced pressure. The crude product (101.9 g) is chromatographed on SilicAR CC-7 (1000 g, Mallinckrodt) in hexane. Elution with 25% ethyl acetate/hexane gives (2S*,3R*)-3-benzyloxy-1,1-ethylenedioxy-2-(4'-hydroxybutyl)-2-methylcyclohexane as a colorless oil (42.3 g, 88%): ir (neat) 3448 cm$^{-1}$ (OH), nmr (CDCl3)δ1.02 (s, 3H, C$\underline{H}$3), 3.92 (s, 4H, ketal), 4.50 (d of d, J=10 Hz, 2H, -O-C$\underline{H}$2Ph), 7.26 (s, 5H, aromatic).

EXAMPLE I (2S*,3R*)-3-Benzyloxy-1,1-ethylenedioxy-2-methyl-2-(4'-oxobutyl)-cyclohexane A pyridine-chromium trioxide solution [C5H5N (120 g, 1.524 mol) and CrO3 (76.2 g, 0.762 mol)] is prepared in dry methylene chloride (2700 ml) at 0° C. in a nitrogen atmosphere. The cooling bath is removed and celite (300 g) is added at 15° C. At 23° C., the alcohol (2S*,3R*)-3-benzyloxy-1,1-ethylenedioxy-2-(4'-hydroxybutyl)-2-methylcyclohexane (42.3 g, 0.127 mol) in methylene chloride (300 ml) is added. After 1 hour, the mixture is filtered and the celite cake is washed with methylene chloride (10×100 ml) and the solvent is removed at reduced pressure. The residue is diluted with ether (750 ml) and filtered. The solvent is removed at reduced pressure and the resulting crude product (46.0 g) is chromatographed on SilicAR CC-7 (1000 g, Mallinckrodt) in hexane. Elution with 25% ethyl acetate/hexane gives (2S*,3R*)-3-benzyloxy-1,1-ethylenedioxy-2-methyl-2-(4'-oxobutyl)-cyclohexane as a colorless oil (25.4 g, 60%): ir (neat) 1718 cm$^{-1}$ (CHO); nmr (CDCl3)δ1.02 (s, 3H, -C$\underline{H}$3), 3.90 (s, 4H, ketal), 4.46 (d of d, J=10 Hz, 2H, -O-C$\underline{H}$2Ph), 7.23 (s, 5H, aromatic), 9.63 (t, 1H, -CHO).

EXAMPLE J (2S*,3R*)-3-Benzyloxy-1,1-ethylenedioxy-2-methyl-2-(4'-hydroxypentyl)-cyclohexane Methyllithium (63.3 ml, 0.0918 l mol, 1.45 M in ether) is added dropwise to a solution of the aldehyde, (2S*,3R*)-3-benzyloxy-1,1-ethylenedioxy-2-methyl-2-(4'-oxobutyl)-cyclohexane (25.4 g, 0.0765 mol) in ether (1000) at 0° C. in a nitrogen atmosphere. The cooling bath is removed and the mixture is stirred for 0.5 hours at ambient temperature. The mixture is then poured into a cold saturated sodium chloride solution (500 ml). The ether phase is separated and the aqueous phase is extracted with ether (3×100 ml). The ether phases are combined, dried (MgSO4) and the solvent is removed at reduced pressure. The crude product (27.1 g) is chromatographed on SilicAR CC-7 (300 g, Mallinckrodt) in hexane. Elution with 10% ethyl acetate/hexane gives (2S*,3R*)-3-benzyloxy-1,1-ethylenedioxy-2-methyl-2-(4'-hydroxypentyl)-cyclohexane as a colorless oil (25.8 g, 97%).

EXAMPLE K (2S*,3R*)-3-Benzyloxy-1,1-ethylenedioxy-2-methyl-2-(4'-oxopentyl)-cyclohexane A solution of pyridine (70.3 g, 0.89 mol) and chromium trioxide (44.5 g, 0.445 mol) in methylene chloride (1.8 l) in a nitrogen atmosphere is stirred for 45 minutes. Celite (180 g) is added followed by (2S*,3R*)-3-benzyloxy-1,1-ethylenedioxy-2-methyl-2-(4'-hydroxypentyl)-cyclohexane (25.8 g, 0.074 mol) in methylene chloride (100 ml). The mixture is stirred for 90 minutes at 23° C. The mixture is then filtered and the celite cake is washed with methylene chloride (10×200 ml). The filtrate and washings are combined and the solvents are removed under reduced pressure to give a dark oil, which is diluted with ether (750 ml) and filtered. The ether phase is dried (MgSO4) and the solvents are removed at reduced pressure. The crude product (21 g) is chromatographed on SilicAR CC-7 (300 g, Mallinckrodt) in hexane. Elution with 6% ethyl acetate/hexane gives (2S*,3R*)-3-benzyloxy-1,1-ethylenedioxy-2-methyl-2-(4'-oxopentyl)-cyclohexane as a clear colorless oil (15.7 g, 61%): ir (neat) 1712 cm$^{-1}$ (CO); nmr (CDCl3)δ1.106 (s, 3H, -C$\underline{H}$3), 2.04

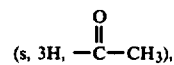

2.30 (m, 2H, -CH2-CO), 3.50

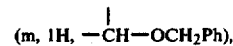

3.98 (s, 4H, ketal), 4.55 (d of d, J=10 Hz, 2H, -O-C$\underline{H}$2Ph), 7.20 (s, 5H, aromatic).

EXAMPLE L (2S*,3R*)-3-Benzyloxy-1,1-ethylenedioxy-2-methyl-2-(4'-methyl-4'-pentenyl)-cyclohexane A suspension of sodium hydride (10.9 g, 0.227 mol) in dimethylsulfoxide (250 ml) is heated to 70° C. under a nitrogen atmosphere and stirred for 45 minutes. The mixture is cooled to 25° C. and methyltriphenylphosphonium iodide (91.7 g, 0.227 mol) in dimethylsulfoxide (100 ml) is added. The mixture is stirred for 30 minutes, (2S*,3R*)-3-benzyloxy-1,1-ethylenedioxy-2-methyl-2-(4'-oxopentyl)-cyclohexane (15.7 g, 0.045 mol) in dimethylsulfoxide (50 ml) is added and the mixture is heated to 60°0 C. After 4 hours, the reaction mixture is cooled and added to saturated sodium chloride (1000 ml) and extracted with ether (5×200 ml). The ether layers are combined, dried (MgSO4) and the solvent is removed under reduced pressure. The crude product (24.1 g) is chromatographed on SilicAR CC-7 (300 g, Mallinckrodt) in hexane. Elution with 4% ethyl acetate/hexane gives (2S*,3R*)-3-benzyloxy-1,1-ethylenedioxy-2-methyl-2-(4'-methyl-4'-pentenyl)-cyclohexane as a light yellow oil (14.3 g, 92%): ir (neat) 1638 cm$^{-1}$ (C=C), nmr (CDCl3)δ1.06 (s, 3H, C$\underline{H}$3), 3.40

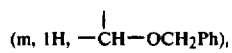

4.50 (d of d, J=10 Hz, 2H, -O-C$\underline{H}$2Ph), 4.61

(broad s, 2H, —C̲=CH₂), 7.30 (s, 5H, aromatic).

EXAMPLE M (2S*,3R*)-3-Benzyloxy-1,1-ethylenedioxy-2-methyl-2-(4'-methyl-5'-hydroxypentyl)-cyclohexane To a solution of 9-borabicyclononane (10.1 g, 0.083 mol) in tetrahydrofuran (600 ml) at 0° C. is added a solution of (2S*,3R*)-3-benzyloxy-1,1-ethylenedioxy-2-methyl-2-(4'-methyl-4'-pentenyl)-cyclohexane (14.3 g, 0.0416 mol) in tetrahydrofuran (150 ml). The cooling bath is removed and the reaction mixture stirred for 3 hours at 25° C. The reaction mixture is decomposed at 0° C. by adding 3 N sodium hydroxide (33 ml, 0.105 mol) followed by 30% hydrogen peroxide (47.6 g, 0.42 mol). The mixture is poured into saturated sodium chloride (1000 ml) and extracted with ether (5×300 ml). The extracts are combined, dried (MgSO₄) and the solvent is removed under reduced pressure. The crude product (20.1 g) is chromatographed on SilicAR CC-7 (250 g, Mallinckrodt) in hexane. Elution with 8% ethyl acetate/hexane gives (2S*,3R*)-3-benzyloxy-1,1-ethylenedioxy-2-methyl-2-(4'-methyl-5'-hydroxypentyl)-cyclohexane as a clear colorless oil (13.9 g, 91%): nmr (CDCl₃)δ0.86

(d, J=6 Hz, 3H, —C̲H—CH₃), 1.08 (s, 3H, C̲H₃), 3.42

(broad d, 3H, HO—CH₂—C̲H— and OH), 3.98 (s, 4H, ketal), 4.52 (d of d, 2H, Ph-C̲H₂-O-), 7.20 (s, 5H, aromatic).

EXAMPLE N (2S*,3R*)-3-Benzyloxy-2-methyl-2-(4'-methyl-5'-hydroxypentyl)-cyclohexanone A mixture of (2S*,3R*)-3-benzyloxy-1,1-ethylenedioxy-2-methyl-2-(4'-methyl-5'-hydroxypentyl)-cyclohexane (13.9 g, 0.0384 mol), acetone (150 ml), water (20 ml) and 0.002 N sulfuric acid (50 ml) is refluxed for 18 hours under a nitrogen atmosphere. The reaction mixture is cooled, the acetone evaporated under reduced pressure and the aqueous layer extracted with ether (3×500 ml). The combined organic layers are washed with saturated sodium bicarbonate (100 ml), saturated sodium chloride (2×200 ml) and dried (MgSO₄). The solvents are removed to afford (2S*,3R*)-3-benzyloxy-2-methyl-2-(4'-methyl-5'-hydroxypentyl)-cyclohexanone (crude product, 12.2 g, 100%): ir (neat) 3484 (OH), 1709 cm⁻¹ (CO); nmr (CDCl₃)δ0.88 (d, J=6 Hz, 3H, -CH-C̲H₃), 1.08 (s, 3H, C̲H₃), 3.42

(m, 4H, HO—C̲H₂—C̲H—, OH and —C̲H—O—CH₂Ph), 4.50 (d of d, J=10 Hz, 2H, Ph-C̲H₂-O-), 7.2 (s, 5H, aromatic).

EXAMPLE O (2S*,3R*)-3-Benzyloxy-2-methyl-2-[4'-methyl-5'-(tetrahydropyran-2''-yloxy)-pentyl]-cyclohexanone A mixture of the alcohol (2S*,3R*)-3-benzyloxy-2-methyl-2-(4'-methyl-5'-hydroxypentyl)-cyclohexanone (12.2 g, 0.038 mol), dihydropyran (4.8 g, 0.057 mole) and p-toluenesulfonic acid (100 mg) in anhydrous ether (150 ml) is stirred at 24° C. under a nitrogen atmosphere for 18 hours. The mixture is then diluted with ether (500 ml), washed with sodium bicarbonate, water and saturated sodium chloride, dried (MgSO₄) and evaporated in vacuo to give 14.3 g of a yellow oil. The oil is chromatographed on silicAR CC-7 (220 g, Mallinckrodt) in hexane. Elution with 5–10% ethyl acetate/hexane gives (2S*,3R*)-3-benzyloxy-2-methyl-2-[4'-methyl-5'-(tetrahydropyran-2''-yloxy)-pentyl]-cyclohexanone as a colorless oil (14.3 g, 88%); nmr (CDCl₃)δ0.83

(d, J=6 Hz, —3H, —C̲H—CH₃), 1.10 (s, 3H, C̲H₃), 4.40 (d of d, J=10 Hz, 2H, -O-C̲H₂Ph), 4.49

(broad s, 1H, —O—C̲H—CO—), 7.20 (s, 5H, aromatic).

EXAMPLE P (2S*,3R*)-3-Benzyloxy-2-methyl-2-[4'-methyl-5'-(tetrahydropyran-2''-yloxy)-pentyl]-1-oxacycloheptan-7-one A solution of (2S*,3R*)-3-benzyloxy-2-methyl-2-[4'-methyl-5'-(tetrahydropyran-2''-yloxy)-pentyl]-cyclohexanone (7.6 g, 0.0189 mol), sodium acetate (1.64 g, 0.02 mol), m-chloroperoxybenzoic acid 85% (4.97 g, 0.0246 mole) and distilled methylene chloride (300 ml) is heated at reflux under a nitrogen atmosphere for 17 hours. The solution is cooled and filtered and the filtrate is washed with saturated sodium bicarbonate, saturated sodium chloride and dried (MgSO₄). The solvent is removed under reduced pressure and the crude product (8.2 g) chromatographed on SilicAR CC-7 (150 g, Mallinckrodt) in hexane. Elution with 10% ethyl acetate/hexane gives recovered (2S*,3R*)-3-benzyloxy-2-methyl-2-[4'-methyl-5'-(tetrahydropyran-2''-yloxy)-pentyl]-cyclohexanone (2.8 g) while 15% ethyl acetate/hexane gives the desired lactone (2S*,3R*)-3-benzyloxy-2-methyl-2-[4'-methyl-5'-(tetrahydropyran-2''-yloxy)-pentyl]-1-oxacycloheptan-7-one 3.5 g, 70% based on the recovery of the starting ketone): nmr (CDCl₃)δ0.95 (d, J=6 Hz, 3H, -CH-C̲H₃), 1.42 (s, 3H -CH₃), 2.62 (m, 2H, -O-CO-CH₂-CH₂-), 4.60 (d of d, J=10 Hz, 2H, -O-CH₂-Ph), 7.22 (s, 5H, aromatic).

EXAMPLE Q (2S*,3R*)-Diethyl-[3-benzyloxy-2-methyl-2-(4'-methyl-5'-(tetrahydropyran-2''-yloxy)-pentyl)-3(H), 4,5-dihydro oxepinyl]-7-phosphate To a lithium diisopropylamide solution [prepared from n-butyllithium in hexane (18.2 ml, 0.0285 mol) and diisopropylamine (2.88 g, 0.0285 mol)] in dry tetrahydrofuran (100 ml) with hexamethylphosphoramide (5.1 g, 0.0285 mol) cooled to −78° C. is added dropwise a solution of (2S*,3R*)-3-benzyloxy-2-methyl-2-[4'-methyl-5'-(tetrahydropyran-2''-yloxy)-pentyl]-1-oxacycloheptan-7-one (7.9 g, 0.019 mol) in dry tetrahydrofuran (50 ml). After stirring for 45 minutes, tetramethylethylenediamine (50 ml) is added followed by diethylchlorophosphate (4.92 g, 0.0285 mol) in tetrahydrofuran (50 ml). The cooling bath is removed and stirring at room temperature is maintained for 0.5 hours. The reaction mixture is poured into pH 7 buffer (250 ml) and extracted with ether (5×100 ml). The ether phases are combined, dried (MgSO4) and the solvent removed under reduced pressure. The crude product (15.3 g) is chromatographed on SilicAR CC-7 (200 g, Mallinckrodt) in hexane. Elution with 20% ethyl acetate/hexane gives (2S*,3R*)-diethyl-[3-benzyloxy-2-methyl-2-(4'-methyl-5'-(tetrahydropyran-2''-yloxy)pentyl)-3(H), 4,5-dihydro oxepinyl]-7-phosphate as a clear light yellow oil (8.92 g, 85%): nmr (CDCl3)δ1.00 (d, J=6 Hz, 3H, -CH-CH3), 1.20 (s, 3H, -CH3), 4.98

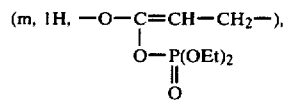

7.30 (s, 5H, aromatic).

EXAMPLE R (2S*,3R*)-3-Hydroxy-2-methyl-2-[4'-methyl-5'-(tetrahydropyran-2''-yloxy)-pentyl]-6-oxepene To a freshly distilled solution of ammonia (450 ml) cooled to −78° C. is added in an argon atmosphere t-butyl alcohol (21.4 g, 0.29 mol). The cooling bath is removed and (2S*,3R*)-diethyl-[3-benzyloxy-2-methyl-2-(4'-methyl-5'-(tetrahydropyran-2''-yloxy)-pentyl)-3(H), 4,5-dihydro oxepinyl]-7-phosphate (8.92 g, 0.0161 mol) in tetrahydrofuran (112 ml) is added. Freshly cut sodium metal (2.22 g, 0.0966 mol) is added in small pieces at −33° C. The resulting blue solution is stirred for 0.5 hours and quenched by adding ether (450 ml) followed by water (100 ml). The ammonia is evaporated at room temperature and the mixture is poured into pH 7 buffer (1000 ml) and ether (250 ml). The ether layer is separated and the water phase is extracted with ether (5×100 ml). The ether phases are combined, washed with saturated sodium chloride (500 ml), dried (MgSO4) and the solvent is removed under reduced pressure. The crude product (5.2 g) is chromatographed on SilicAR CC-7 (75 g, Mallinckrodt) in hexane. Elution with 10% ethyl acetate/hexane gives (2S*,3R*)-3-hydroxy-2-methyl-2-[4'-methyl-5'-(tetrahydropyran-2''-yloxy)-pentyl]-6-oxepene as a clear light yellow oil (2.7 g, 54%): ir (neat) 3481 (OH), 1650 cm⁻¹ (O-C=C), nmr (CDCl3)δ0.93

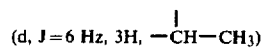

1.22 (s, 3H, CH3), 4.78

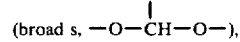

4.92 (m, 1H, -O-CH=CH-), 6.01 (m, 1H, -O-CH=CH-).

EXAMPLE S (2S*,3R*)-3-Benzyloxy-2-methyl-2-[4'-methyl-5'-(tetrahydropyran-2''-yloxy)-pentyl]-6-oxepene To a suspension of sodium hydride (830 mg, 0.0173 mol) in benzene (50 ml) is added (2S*,3R*)-3-hydroxy-2-methyl-2-[4'-methyl-5'-(tetrahydropyran-2''-yloxy)-pentyl]-6-oxepene (2.7 g, 0.00865 mol) in benzene (25 ml) in a nitrogen atmosphere. After 0.5 hours, benzyl bromide (3.0 g, 0.0173 mol) in benzene (25 ml) is added. The mixture is refluxed for 16 hours, cooled and poured into saturated sodium chloride (200 ml). The aqueous layer is extracted with ether (5×75 ml). The organic phases are combined, dried (MgSO4) and the solvents are removed under reduced pressure. The crude product (3.6 g) is chromatographed on SilicAR CC-7 (75 g, Mallinckrodt) in hexane. Elution with 7% ethyl acetate/hexane gives (2S*,3R*)-3-benzyloxy-2-methyl-2-[4'-methyl-5'-(tetrahydropyran-2'-yloxy)-pentyl]-6-oxepene as a clear colorless oil (3.25 g; 93%): nmr (CDCl3)δ0.92

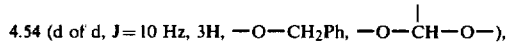

4.94 (m, 1H, -O-CH=CH-), 6.00 (d, J=6 Hz, 1H, -O-CH=CH-), 7.25 (s, 5H, aromatic).

EXAMPLE T (2S*,3R*)-3-Benzyloxy-2-methyl-2-[4'-methyl-5'-(tetrahydropyran-2''-yloxy)-pentyl]-oxepan-6-ol To a solution of (2S*,3R*)-3-benzyloxy-2-methyl-2-[4'-methyl-5'-(tetrahydropyran-2''-yloxy)-pentyl]-6-oxepene (3.25 g, 0.0081 mol) in tetrahydrofuran (60 ml) at 0° C. in a nitrogen atmosphere is added diborane (10.8 ml, 0.0108 mol, 1M solution in tetrahydrofuran). The cooling bath is removed and the mixture is stirred for 2 hours at 25° C. The reaction mixture is then quenched by adding 3 N sodium hydroxide (5.4 ml, 0.021 mol) followed by 30% hydrogen peroxide (3.8 g, 3.6 ml, 0.111 mol). The reaction mixture is stirred at 25° C. for 1.5 hours, then poured into saturated sodium chloride (250 ml) and ether (150 ml). The ether layer is separated and the aqueous phase is extracted with ether (7×75 ml). The ether phases are combined, dried (MgSO4) and the solvents are removed at reduced pressure. The crude product (4.1 g) is chromatographed on SilicAR CC-7 (50 g, Mallinckrodt) in hexane. Elution with 25% ethyl acetate/hexane gives (2S*,3R*)-3-benzyloxy-2-methyl-2-[4'-methyl-5'-(tetrahydropyran-2''-yloxy)-pentyl]-oxepan-6-ol as a clear colorless oil (2.4 g, 71%): ir (neat) 3500 cm⁻¹ (OH): nmr (CDCl3)δ0.92 (d, J=6 Hz, 3H, -CH-CH3), 7.25 (s, 5H, aromatic); the compound is a mixture of epimeric alcohols as shown by thin layer chromatography, ethyl acetate/hexane (40:60).

What is claimed is:

1. The process for the preparation of a compound selected from the group consisting of

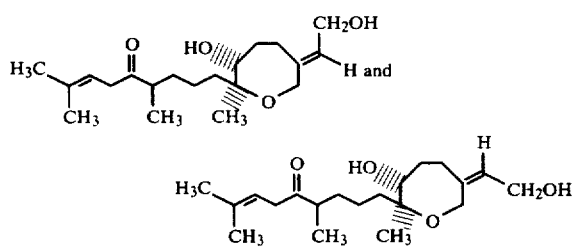

which comprises reacting a compound of the formula

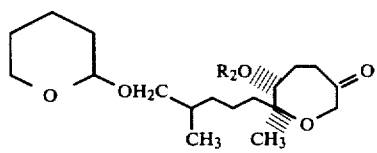

with ethylene glycol to form a ketal of the formula

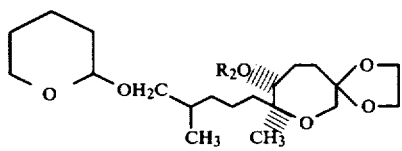

reacting the product formed with sodium in liquid ammonia to form an alcohol of the formula

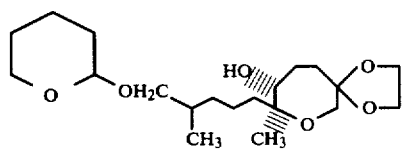

reacting the alcohol with t-butyldiphenylsilyl chloride in the presence of imidazole to form a compound of the formula

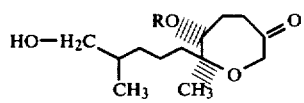

reacting the alcohol formed with dihydropyran and an acid selected from P-toluenesulfonic acid and camphorsulfonic acid to form a compound of the formula

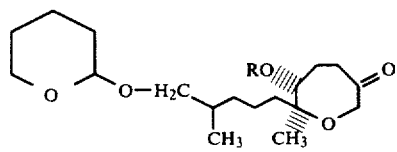

reacting the ketone with triethylphosphonoacetate to form a mixture of isomers having the formulas

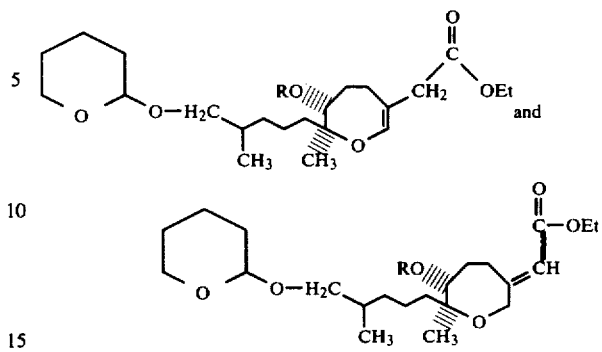

reacting the mixture with lithium aluminum hydride to form a mixture of alcohols having the formulas

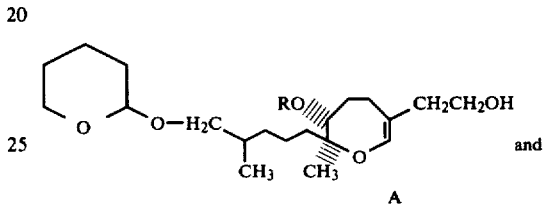

A

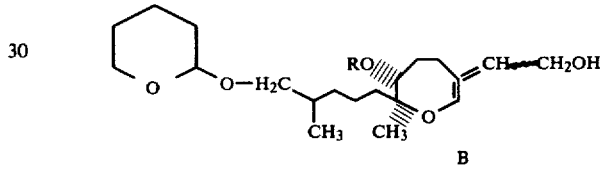

B separating the alcohols, and reacting the alcohol B with t-butyldiphenylsilyl chloride to form a compound of the formula

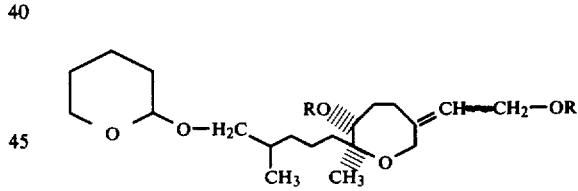

reacting the product with acetic acid to form an alcohol of the formula

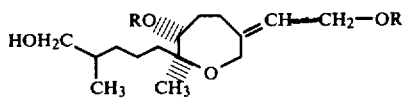

reacting the alcohol with chromium trioxide to form an aldehyde of the formula

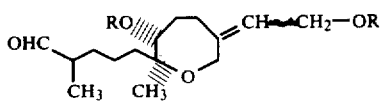

reacting the aldehyde with an acetylenic Grignard reagent prepared from

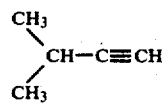

to form a compound of the formula

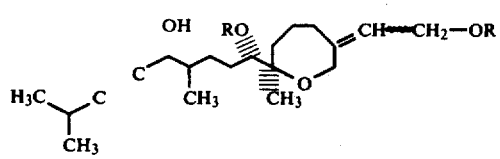

reacting the product with lithium aluminum hydride to form a compound of the formula

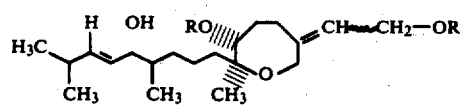

reacting the alcohol formed with an oxidizing agent selected from chromium trioxide and manganese dioxide to form a ketone of the formula

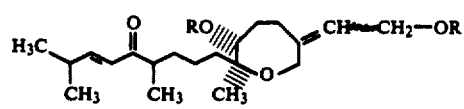

reacting the ketone with potassium t-butoxide followed by treatment with acetic acid to form a compound of the formula

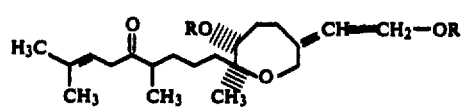

reacting the product with sodium borohydride to form a compound of the formula

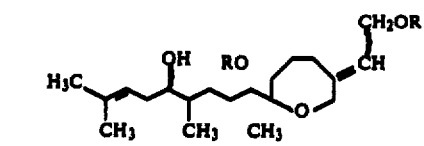

reacting the product formed with dihydropyran and an acid selected from P-toluenesulfonic acid and camphorsulfonic acid to form a compound of the formula

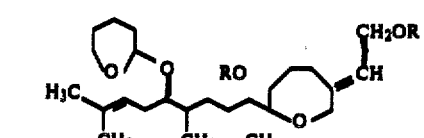

reacting the product formed with tetrabutylammonium fluoride to form a mixture of compounds of the formula

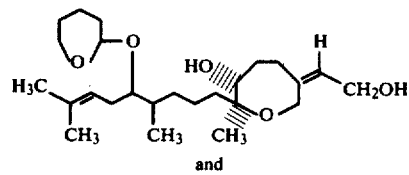

and

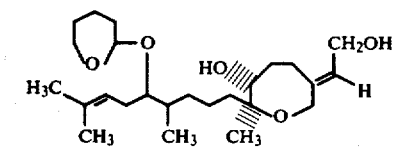

separating the compounds in the mixture, and then (a) reacting compound A with an esterifying agent selected from a lower alkyl anhydride or alkanoyl halide having 2-5 carbon atoms to form an ester of the formula

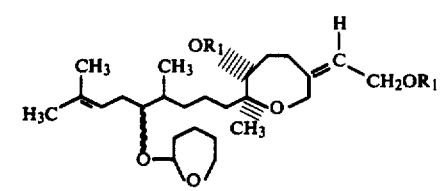

treating the product with an acid selected from acetic acid, P-toluenesulfonic acid and camphorsulfonic acid to form an alcohol of the formula

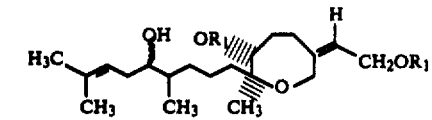

treating the alcohol formed with chromium trioxide to form a ketone of the formula

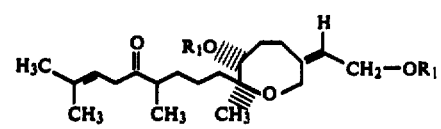

and reacting the product formed with tetrabutylammonium hydroxide to form a compound of the formula

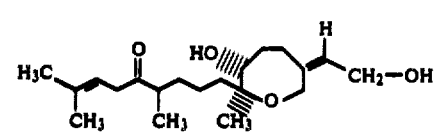

and (b) reacting compound B with an esterifying agent selected from a lower alkyl anhydride or alkanoyl halide having 2-5 carbon atoms to form an ester of the formula

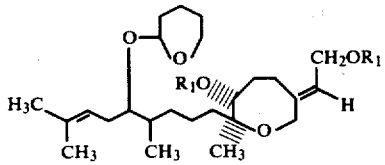

treating the product formed with an acid selected from acetic acid, P-toluenesulfonic acid and camphorsulfonic acid to form an alcohol of the formula

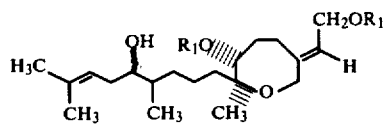

treating the alcohol formed with chromium trioxide to form a ketone of the formula

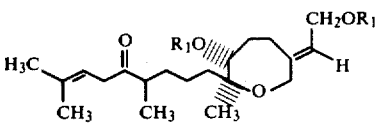

and reacting the product formed with tetrabutylammonium hydroxide to form a compound of the formula

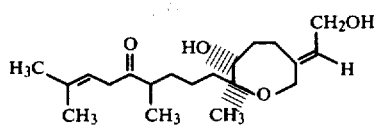

wherein R is a t-butyldiphenylsilyl group, $R_1$ is lower alkanoyl having 2-5 carbon atoms and $R_2$ is selected from the group consisting of benzyl, p-nitrobenzyl and p-methylbenzyl.

2. The process of claim 1 wherein the esterifying agent is acetic anhydride.

3. The process of claim 1 wherein $R_1$ is acetyl and $R_2$ is benzyl.

* * * * *